(12) United States Patent
Xu et al.

(10) Patent No.: US 8,217,173 B2
(45) Date of Patent: Jul. 10, 2012

(54) FLUORIDE-RELEASING COMPOSITIONS

(75) Inventors: Xiaoming Xu, Mandeville, LA (US); Shailaja Jayaramachandran, Arlington, MA (US); Liang Chen, Schaumburg, IL (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 435 days.

(21) Appl. No.: 12/526,321

(22) PCT Filed: Feb. 12, 2008

(86) PCT No.: PCT/US2008/053683
§ 371 (c)(1),
(2), (4) Date: Sep. 2, 2009

(87) PCT Pub. No.: WO2008/100907
PCT Pub. Date: Aug. 21, 2008

(65) Prior Publication Data
US 2010/0261902 A1    Oct. 14, 2010

Related U.S. Application Data

(60) Provisional application No. 60/889,653, filed on Feb. 13, 2007.

(51) Int. Cl.
*C07F 7/00* (2006.01)
*C07D 401/12* (2006.01)

(52) U.S. Cl. ............... 546/10; 546/261; 546/2; 556/55; 560/129

(58) Field of Classification Search .................. 546/10, 546/2, 261; 556/55; 560/129
See application file for complete search history.

(56) References Cited

U.S. PATENT DOCUMENTS

| | | | | |
|---|---|---|---|---|
| 4,871,786 A | 10/1989 | Aasen et al. | ................... | 523/113 |
| 5,624,901 A | 4/1997 | Raymond et al. | ................ | 514/17 |
| 6,391,286 B1 | 5/2002 | Mitra et al. | ...................... | 424/54 |
| 6,703,518 B1 | 3/2004 | Xu et al. | ......................... | 556/56 |
| 6,932,960 B2 | 8/2005 | Liu | .............................. | 424/1.65 |

FOREIGN PATENT DOCUMENTS

WO    WO/00/69394    11/2000

OTHER PUBLICATIONS

Chikuma, M. et al., "Selective Sorption of Fluoride Ions by Anion-Exchange Resin Modified with Alizarin Fluorine Blue-Praseodymium (III) Complex," *Reactive Polymers*, vol. 13, pp. 131-138 (1990).
Fenton, D.E. et al.,, "Binuclear Complexes of Tetraketones," *Inorganica Chimica Acta*, vol. 58, pp. 83-88 (1982).
Glasspoole, E. et al.,, "A Fluoride-Releasing Composite for Dental Applications," *Dental Materials*, vol. 17, pp. 127-133 (2001).
Imazato, S. et al., "Antibacterial Activity and Bonding Characteristics of an Adhesive Resin Containing Antibacterial Monomer MDPB," Dent Mater, vol. 19, pp. 313,319 (2003).
Imazato, S., "Antibacterial properties of resin composites and dentin bonding systems," *Dent. Mater*, vol. 19, pp. 449-457 (2003).
Imazato, S. et al.,, "Incorporation of antibacterial monomer MDPB into dentin prime,"..*Journal of Dental Research*, vol. 76, pp. 768-722 (1997).
Imazato, S. et al.,, "Incorporation of bacterial inhibitor into resin composite," *Journal of Dental Research*, vol. 73, pp. 1437-1443 (1994).
Kenawy, E-R et al.,, "The Chemistry and Applications of Antimicrobial Polymers: A State-of-the-Art Review," *Biomacromolecules*, vol. 8, No. 5, pp. 1359-1384 (2007).
Rawls, H. et al.,, "Esthetic Materials with Active Agent Control Release Capabilities and Their Future Roles," pp. 130-135 in *Symposium on Esthetic Restorative Materials*, 1991 (American Dental Association 1993).
Rawls, H., "Preventive Dental Materials: Sustained Delivery of Fluoride and Other Therapeutic Agents," *Advances in Dental Research*, vol. 5, pp. 50-55 (Dec. 1991).
Streater, M. et al.,, "Novel 3-hydroxy-2 (1H)-pyridinones. Synthesis, Iron (III)-chelating properties, and biological activity," *J. Med. Chem*, vol. 33, pp. 1749-1755 (1990).
Uhlir, L.C. et al.,, "Specific sequestering agents for the actinides. 21. Synthesis and initial biological testing of octadentate mixed catecholate-hydroxypyridinonate ligands," *J. Med. Chem.*, vol. 36, pp. 504-509 (1993).
White, D.L. et al.,, "Synthesis and initial biological testing of polydentate oxohydroxy-pyridine-carboxylate ligands," *J. Med. Chem*, vol. 31, pp. 11-18 (1988).
Xu, X. et al.,, "Formulation and characterization of a novel fluoride-releasing dental composite," *Dental Materials*, vol. 22, No. 11, pp. 1014-1023 (2006).
Xu, X. et al.,, "Synthesis and Characterization of a Novel, Fluoride-Releasing Dimethacrylate Monomer and Its Dental Composite" *Journal of Polymer Science:* Part A: Polymer Chemistry, vol. 42, pp. 985-995 (2004).
Xu, X. et al.,, "Synthesis and Characterization of Novel Fluoride-Releasing Monomers 2: Dimethacrylates Containing Bis(aminodiacetic acid) and Their Ternary Zirconium-Fluoride Complexes," *Journal of Polymer Science A: Polymer Chemistry*, vol. 43, pp. 3153-3166 (2005).
Xu, J. et al.,, "Synthesis and Initial Evaluation for In Vivo Chelation of Pu(IV) of a Mixed Octadentate Spermine-Based Ligand Containing 4-Carbamoyl-3-hydroxy-1-methyl-2(1H)-pyridinone and 6-Carbamoyl-1-hydroxy-2(1H)-pyridinone," *J. Med. Chem.*, vol. 45, pp. 3963-3971 (2002).
Xu, X. et al.,, "Synthesis of New Chelating Monomers Containing Bis(Carboxymethyl)-L-Lysine and Their Zirconium Fluoride Complexes," Abstract, 231st ACS National Meeting, Atlanta, GA (Mar. 26-30, 2006).

(Continued)

*Primary Examiner* — Charanjit Aulakh
(74) *Attorney, Agent, or Firm* — John H. Runnels; Bonnie J. Davis

(57) ABSTRACT

Chelating monomers and fluoride-releasing compositions are disclosed that may be incorporated into dental composite restorative materials, dental bonding agents or other dental materials, to produce materials with high fluoride release rates, and high fluoride recharge capability. Such dental restorative materials may help reduce the level of dental caries in patients, particularly the level of caries occurring on the margins of the restorative materials.

12 Claims, No Drawings

OTHER PUBLICATIONS

Xu, X. et al.,, "Synthesis of New Chelating Monomers Containing Bis(Carboxymethyl)-L-Lysine and Their Zirconium Fluoride Complexes," Polymer Preprints (Proceedings of 231st ACS National Meeting, Atlanta, GA,) vol. 47, No. 1, pp. 335-336 (Mar. 26-30, 2006).

Xu, X. et al.,, "Synthesis of new fluoride-releasing dental monomer containing 1,2-hydroxypyridinones and zirconium fluoride complexes," Polymer Preprints (Proceedings of 231st ACS National Meeting, Atlanta, GA), vol. 47, No. 1, pp. 337-338 (Mar. 26-30, 2006).

Xu, et al.,, "Synthesis of new fluoride-releasing dental monomer containing 1,2-hydroxypyridinones and zirconium fluoride complexes," Abstract, 231st ACS National Meeting, Atlanta, GA (Mar. 26-30, 2006).

Yuchi et al.,, "Complexes of Hard Metal Ions with Amine-N-Polycarboxylates as Fluoride Receptors," *Bull. Chem. Soc. Jpn.*, vol. 69, pp. 3173-3177 (1996).

Zimmerman, B. et al.,, "Prevention of in vitro Secondary Caries with an Experimental Fluoride-Exchanging Restorative Resin," J. Dental Res., vol. 63, pp. 689-692 (1984).

FLUORIDE-RELEASING COMPOSITIONS

This is the United States national stage of international application PCT/US2008/053683, international filing date 12 Feb. 2008, which claims the benefit of the 13 Feb. 2007 filing date of U.S. provisional patent application 60/889,653 under 35 U.S.C. §119(e).

The development of this invention was partially funded by the Government under grant number 1P20RR020160 awarded by the National Institutes of Health, Center of Biomedical Research Excellence. The Government has certain rights in this invention.

This invention pertains to compositions that release fluoride ion and that may be readily recharged with additional fluoride ion. These compositions are useful, for example, in dental composites, dental bonding agents, and other resin-based dental materials.

Fluoride is the most widely used agent to prevent dental caries (tooth decay). Tooth decay can occur on the margins of dental restorations. Such recurring or secondary caries is a frequent cause for failure of dental restorations. Fluoride-releasing restorative materials have been used to try to reduce recurrent caries at restoration margins. The effectiveness of such fluoride-releasing materials varies widely. Fluoride-releasing materials generally fall into one of four categories: glass ionomers, resin-modified glass ionomers, polyacid-modified composite resins (so-called "compomers") and fluoride-releasing composite resins. In general, materials with higher levels of fluoride release have tended to have poorer mechanical properties (e.g., a lower compressive strength). High fluoride-releasing materials (glass ionomers and resin-modified glass ionomers) have therefore been used clinically primarily to restore decayed, but non-biting areas.

Composite resins have been widely used in restorative dentistry because they have high strength, good wear resistance, and excellent esthetics, but they release relatively small amounts of fluoride, and have low fluoride-recharge capacity. There is an unfilled need for dental composite resins with high strength, good wear resistance, high fluoride release rates, and high fluoride recharge capability, i.e., the ability to take up fluoride from an aqueous solution containing a high concentration of fluoride (e.g., a fluoridated toothpaste, topical fluoride agent, or mouthwash).

Composite resins require bonding agents to bond to tooth structure. Current dental bonding agents have little fluoride-releasing and recharging capabilities and form a barrier hindering the transport of fluoride from the restorative materials into the tooth structures. Sealants, which are resins with or without fillers, have been used to fill the pits and fissures in posterior teeth, but many dentists are reluctant to use sealants because they fear that caries in sealed carious pits or fissures may progress. Thus there is an unfilled need for dental bonding agents and sealants that have excellent adhesion to tooth structures, high fluoride release rates, and high fluoride recharge capability.

Currently, fluoride released from resin-based dental restorative materials comes from four main sources: (1) a soluble free salt, such as NaF, KF, or $SnF_2$ added to the material; (2) fluoride-releasing glass fillers such as fluoroaluminosilicate glass, or sparingly soluble inorganic salts such as $YbF_3$; (3) polymer molecules containing an anion-exchangeable fluoride moiety such as $—N(CH_3)_2HF$; or (4) organic fluoride sources such as those from alkylonium tetrafluoroborate.

U.S. Pat. No. 6,391,286 discloses fluoride releasing materials for use in dental compositions, having the formula $M(G)_g(F)_n$ or $M(G)_g(ZF_m)_n$, where M is an element capable of forming a cationic species and having a valence of 2 or more; G is an organic chelating moiety capable of complexing with the element M; Z is hydrogen, boron, nitrogen, phosphorus, sulfur, antimony, or arsenic; F is fluoride; and g, m, and n are each at least 1.

U.S. Pat. No. 4,871,786 discloses dental compositions employing one or more substantially soluble organic compounds that serve as fluoride sources by incorporating tetrafluoroborate. Preferred non-polymerizable fluoride sources were said to be compounds of the formula: $R_n$-$M^+$ $BF_4^-$ where M is I, N, P, or S; n is 2, 3, or 4, depending on the identity of M; and R is one of several specified types of substituted or unsubstituted hydrocarbon chains. Preferred polymerizable fluoride sources were said to be compounds of the formula: $R_{(n-1)}$-$M^+(L)$ $BF_4^-$ where the other symbols were as previous stated, and L is an organic ligand comprising a moiety capable of polymerization via a cationic, condensation, or free radical mechanism.

U.S. Pat. No. 6,703,518 discloses fluoride releasing compositions comprising chelating monomers and ternary metal fluoride chelates. For example, the chelating monomers may contain chelating groups of aminodiacetic acids, amidodiacetic acids, or phosphonic acids. The chelating monomers may also include short-chain monomers containing vinylbenzyl, methacrylate, or bis(carboxymethyl)-L-lysine.

Published international patent application WO 00/69394 discloses what were said to be stable dental materials comprising a compound having only one acid functionality and at least one polymerizable functionality. The material does not contain deleterious quantities of polyacid compounds. The material also contains a fluoride source containing polyvalent metal ions, and a photopolymerization initiator.

A. Yuchi et al., "Complexes of Hard Metal Ions with Amine-N-Polycarboxylates as Fluoride Receptors," *Bull. Chem. Soc. Jpn.*, vol. 69, pp. 3173-3177 (1996) discloses studies of equilibria in the reaction of hard metal complexes ($M^{m+}$: $Al^{3+}$, $Zr^{4+}$, $Hf^{4+}$, $Th^{4+}$; $H_nL$: amine-N-polycarboxylic acid) with fluoride. The zirconium (IV) complex of N-methyliminodiacetic acid was reported to be an excellent fluoride receptor.

M. Chikuma et al., "Selective Sorption of Fluoride Ions by Anion-Exchange Resin Modified with Alizarin Fluorine Blue-Praseodymium (III) Complex," *Reactive Polymers*, vol. 13, pp. 131-138 (1990) discloses a resin for the selective sorption of fluoride ion, prepared from an anion exchange resin, Amberlite™ IRA 400, and a praseodymium (III) complex of alizarin fluorine blue.

H. Rawls et al., "Esthetic Materials with Active Agent Control Release Capabilities and Their Future Roles," pp. 130-135 in *Symposium on Esthetic Restorative Materials, 1991* (American Dental Association 1993) provides a review of dual-purpose dental restorative materials: those that can both serve the needs of esthetic dentistry and that can also serve as sustained-release sources of therapeutic agents, such as fluoride. See also H. Rawls, "Preventive Dental Materials: Sustained Delivery of Fluoride and Other Therapeutic Agents," *Advances in Dental Research*, vol. 5, pp. 50-55 (December 1991).

E. Glasspoole et al., "A Fluoride-Releasing Composite for Dental Applications," *Dental Materials, vol.* 17, pp. 127-133 (2001) discloses the incorporation of an organic fluoride material, tetrabutylammonium tetrafluoroborate, into a hydrophilic monomer system made of 2,2-bis[4-(2-hydroxy-3-methacroyloxypropoxy)phenyl]-propane and 2-hydroxyethyl methacrylate. The resulting fluoride release rates were reported to exceed those of several glass ionomer materials that were also tested.

B. Zimmerman et al., "Prevention of in vitro Secondary Caries with an Experimental Fluoride-Exchanging Restorative Resin," *J. Dental Res.*, vol. 63, pp. 689-692 (1984) reported clinical observations in which experimental composite resins that released fluoride by ion exchange were seen to reduce the incidence of caries in immediately adjacent areas, as compared to the rates of caries observed when non-fluoride-containing materials were used.

Several publications by one or more of the present inventors have reported the synthesis of the fluoride-releasing dimethacrylate monomers containing aminodiacetic acids or amidodiacetic acids and their applications in fluoride-releasing dental composites. See X. Xu et al., "Synthesis and Characterization of a Novel, Fluoride-Releasing Dimethacrylate Monomer and Its Dental Composite" *Journal of Polymer Science: Part A: Polymer Chemistry*, 2004; 42:985-995; X. Xu et al., "Synthesis and Characterization of Novel Fluoride-Releasing Monomers 2: Dimethacrylates Containing Bis (aminodiacetic acid) and Their Ternary Zirconium-Fluoride Complexes," *Journal of Polymer Science A: Polymer Chemistry* 2005, 43, 3135-3166; X. Xu et al., "Formulation and characterization of a novel fluoride-releasing dental composite," *Dental Materials* 2006, 22(11): 1014-1023. While these previously-reported compositions are useful, there is still a need for compositions with enhanced stabilities and fluoride recharge capabilities.

Hydroxypyridinones (HOPO), which have adjacent keto and hydroxyl groups, and catechols, which have two adjacent hydroxyl groups, are both bidentate chelating ligands. They can form five-member rings with heavy metals such as Fe (III) and Pu (IV). Multidentate chelating ligands containing two to four HOPO or catechol groups can form highly stable complexes with heavy metals. D. L. White et al., "Synthesis and initial biological testing of polydentate oxohydroxy-pyridine-carboxylate ligands," *J. Med. Chem.* 1988, 31, 11-18, reported the synthesis of water-soluble chelating ligands containing two to four 1,2-hydroxypyridinone (1,2-HOPO) groups. L. C. Uhlir et al., "Specific sequestering agents for the actinides. 21. Synthesis and initial biological testing of octadentate mixed catecholate-hydroxypyridinonate ligands," *J. Med. Chem.* 1993, 36, 504-509, reported the synthesis of mixed catecholate-hydroxypyridinonate ligands and their complexes with Pu (IV). The high binding ability of these ligands for heavy metals allows them to be used to remove actinides such as Pu(IV) from biological systems.

M. Streater et al., "Novel 3-hydroxy-2 (1H)-pyridinones. Synthesis, Iron (III)-chelating properties, and biological activity," *J. Med. Chem.* 1990, 33, 1749-55, and K. N. Raymond et al., "3-hydroxy-2 (1H)-pyridinone chelating agents," U.S. Pat. No. 5,624,901, reported the synthesis of chelating ligands containing 3-hydroxy-2(1H)-pyridinones (2,3-HOPO). J. Xu et al., "Synthesis and Initial Evaluation for In Vivo Chelation of Pu(IV) of a Mixed Octadentate Spermine-Based Ligand Containing 4-Carbamoyl-3-hydroxy-1-methyl-2(1H)-pyridinone and 6-Carbamoyl-1-hydroxy-2(1H)-pyridinone," *J. Med. Chem.* 2002, 45, 3963-3971, reported the synthesis of chelating ligands containing 4-Carbamoyl-3-hydroxy-1-methyl-2(1H)-pyridinone and 6-Carbamoyl-1-hydroxy-2(1H)-pyridinone. These chelating ligands were effective in removing excess Fe (III) from biological systems, with little toxicity.

S. Liu, U.S. Pat. No. 6,932,960 reported the synthesis and pharmaceutical applications of N-substituted 3-hydroxy-4-pyridinones. R. L. Bruening et al., U.S. Pat. Nos. 6,221,476 and 6,432,313, reported hydrophilic polymer membranes containing hydroxypyridinones and their application in removal of metal ions.

Molecules containing β-diketones, particularly aromatic tetraketones with two β-diketones connected by a benzene or pyridine, are strong chelating ligands and can form complexes with many metal ions. See D. E. Fenton et al., "Binuclear Complexes of Tetraketones," *Inorganica Chimica Acta*, 1982, 58, 83-88.

Polymers with antimicrobial (mainly antibacterial and antifungal) activities, generally known as polymeric biocides or antimicrobial polymers, have drawn interest in the fields of biomedical materials and medical implants. See Kenawy E-R et al., The Chemistry and Applications of Antimicrobial Polymers: A State-of-the-Art Review. *Biomacromolecules* 2007; 8(5):1359-1384. Common biocide moieties include quaternary ammonium, pyridinium, phosphonium, and sulfonium salts. The mechanism of action of the quaternary compounds may be direct cationic binding to cell wall components, leading to disruption of the cell wall membrane, and subsequently leakage of cell contents and cell death. To achieve high antimicrobial efficacy, the quaternary salt preferably has at least one long-chain alkyl or substituted alkyl group, and a relatively low tendency to form an ion-pair with the counter ion.

One of the few antibacterial monomers that has been used in dental materials to date is methacryloyloxydodecyl pyridinium bromide (MDPB). See Imazato S. et al., Incorporation of bacterial inhibitor into resin composite. *Journal of Dental Research* 1994; 73:1437-1443, Imazato S, et al., Incorporation of antibacterial monomer MDPB into dentin primer. *Journal of Dental Research* 1997; 76:768-772. The bactericidal activity of the monomer and different dental materials (primer, bonding adhesive, and composite) containing MDPB against oral Streptococci have been studied. See Imazato S, et al., Antibacterial activity and bonding characteristics of an adhesive resin containing antibacterial monomer MDPB. *Dent. Mater.* 2003; 19:313-319, and Imazato S. Antibacterial properties of resin composites and dentin bonding systems. *Dent. Mater.* 2003; 19:449-457. MDPB has been reported to inhibit bacterial growth in uncured resins, in cured resins, and in bonding agents. To incorporate antibacterial activity in a self-etching bonding agent would be of particular clinical importance, because self-etching bonding agents have usually had pH higher than about 2.0, and have not effectively killed acid-resistant bacteria. By contrast, a conventional phosphoric acid (37%) etching gel has pH of 0.8 and effectively kills most bacteria. MDPB has been used in a commercial self-etching bonding agent, Protect Bond™ (Kuraray, Japan).

To the inventors' knowledge, the use of fluoride exchange monomers in combination with antibacterial monomers in dental materials has not previously been reported.

We have discovered novel chelating monomers and ternary metal fluoride chelates (fluoride-releasing monomers). The chelating monomers contain both polymerizable groups and chelating groups, such as bis(carboxymethyl)-L-lysine, hydroxypyridinones, catechols, and aromatic β-diketones. Hydroxypyridinones (HOPOs) and catechols are linked to one another, for example via ether or alkyl groups, to form multidentate chelating ligands. The novel chelating ligands are less hydrophilic than those containing amide-linked HOPO ligands. They typically form more stable ternary metal fluoride chelates than will monomers containing aminodiacetic acids or amidodiacetic acids. The novel chelating monomers and novel fluoride-releasing compositions may, for example, be incorporated into dental composite restorative materials, dental bonding agents, or other dental materials, to produce materials with high fluoride release rates and high fluoride recharge capability.

The new chelating and fluoride-releasing monomers of the present invention include those having the following general formulas, where the formula on the left depicts a chelating monomer, and that on the right depicts a monomer chelated to a metal atom, which in turn is coordinated to one or more fluoride ions:

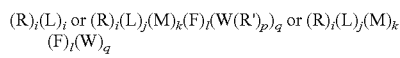

wherein: R is a substituted or unsubstituted aliphatic or aromatic group having 3 to 100 carbon atoms, and having at least one polymerizable group, the polymerizable group being preferably, but not necessarily, located in a terminal position; L is a substituted or unsubstituted aliphatic or aromatic chelating group having 3 to 100 carbon atoms, which is a multidentate (at least a bidentate) ligand; M is a metal atom having a valence of +2 or higher; i, j, k, and l are positive integers from 1 to 4; F is a fluoride atom; W is a counter-ion to maintain the neutrality of the monomer; R' is an optional substituted or unsubstituted aliphatic or aromatic group having 1 to 50 carbon atoms, and having at least one polymerizable group; and p and q are integers from 0 to 4. R' may bind W through a covalent bond, a coordination bond, or ionic bonding.

Preferred embodiments of the invention include one or more of the following options: (1) the use of multiple polymerizable terminal groups in the R (or R') moieties or multiple Rs each with at least one polymerizable terminal group, for example di- or polymethacrylates, to form a cross-linked polymer matrix; (2) including long-chain aliphatic or aromatic groups (10 or more carbon atoms) in the R moieties to reduce hydrophilicity (water sorption) and to increase miscibility with other dental monomers; (3) linking hydroxypyridinones and catechols together, for example through ether or alkyl groups, to form multidentate chelating ligands, which will generally be less hydrophilic than those containing amide-linked HOPO ligands, increasing miscibility with other dental monomers; (4) employing chelating ligands with a total of 3 to 6 "donor" oxygen atoms, wherein the ionized ligands have a nominal valence of −3, −2, or −1, which allows the coordination of one or more additional fluoride ions or ion-pairs containing fluoride (e.g., FH, tetraalkylammonium fluoride, etc); (5) employing quaternary ammonium, pyridinium, phosphonium, or sulfonium cations, to serve both as counter-ions and as antimicrobial agents.

In the general formula above, M is a metal having a valence of +2 or greater. Preferred metals M are those having +3 or +4 valences, particularly those that tend to form colorless complexes with the ligands and with fluoride. For example, M may be $Sn^{+2}$, $Zn^{+2}$, $Sr^{+2}$, $Al^{+3}$, $La^{+3}$, $Ce^{+3}$, $Sb^{+3}$, $Yb^{+3}$, $Ti^{+4}$, $Sn^{+4}$, $Zr^{+4}$, $Ce^{+4}$, or $Th^{+4}$. Particularly preferred is $Zr^{+4}$, because that cation is nontoxic, colorless, and relatively inexpensive, has a high valence, and has a high tendency to form multinucleate complexes with fluoride ions, leading to high fluoride-exchange capacity. In addition, Zr has a high atomic weight, providing radiopacity, a desirable property for dental restorative materials.

W or $W(R')_p$ is a counter-ion to maintain the neutrality of the monomer, for example hydrogen, lithium, sodium, potassium, ammonium, quaternary ammonium, or pyridinium ions. Preferred R' groups contain at least one long-chain (at least 8 carbon atoms) alkyl or substituted alkyl group with antimicrobial activity, more preferably with at least two short-chain substituents (e.g., methyl) to reduce any tendency to form tight ion-pairs with fluoride ion. Preferred $W(R')_p$ include the following examples:

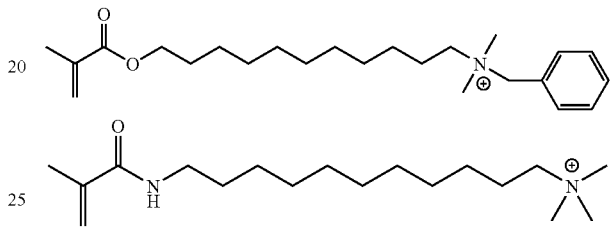

The R and R' groups in the general formula contain at least one polymerizable moiety such as a C=C double bond, an epoxy group, an ethyleneimine group, isocyanides, or thiol. Preferred R groups include the esters of acrylic or methacrylic acid, for example methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate, hydroxypropyl acrylate, hydroxypropyl methacrylate, tetrahydrofurfuryl acrylate, tetrahydrofurfuryl methacrylate, glycidyl acrylate, glycidyl methacrylate, glycerol mono- and di-acrylate, glycerol mono- and di-methacrylate, ethyleneglycol diacrylate, ethyleneglycol dimethacrylate, neopentyl glycol diacrylate, neopentylglycol dimethacrylate, and trimethylolpropane triacrylate.

Other examples of R or R' include vinyl azalactone, vinyl pyrrolidone, styrene, divinylbenzene, urethane acrylates or methacrylates, epoxy acrylates or methacrylates and polyol acrylates or methacrylates, substituted acryl amides and methacrylamides.

Alternatively, the polymerizable component may be a cationically curable material, such as one of the epoxies, oxetanes, oxolanes, cyclic acetals, lactams, lactones, vinyl ethers, and spirocyclic compounds containing one or more oxygen atoms in the ring.

Particularly preferred examples of the R group include one or more of the following structures R1-R13:

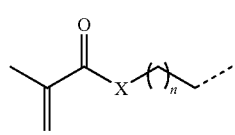

R1

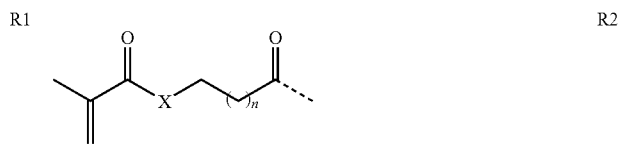

R2

-continued
R3
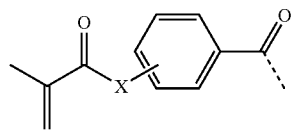
R4
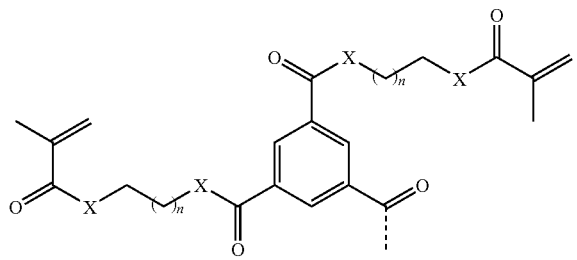
R5
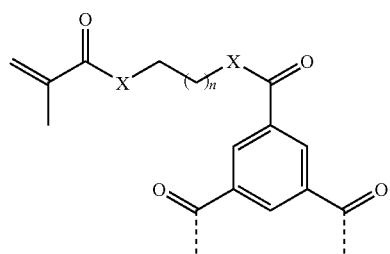
R6
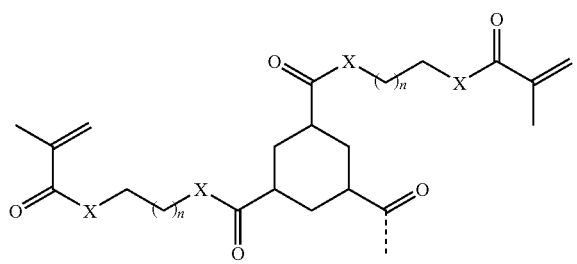
R7
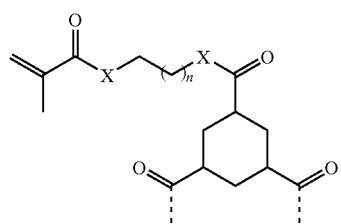
R8
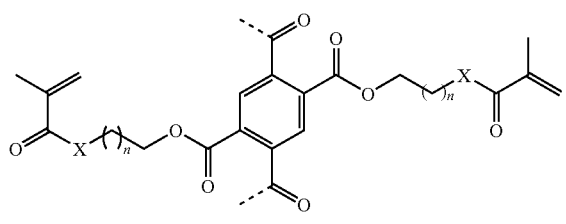
R9
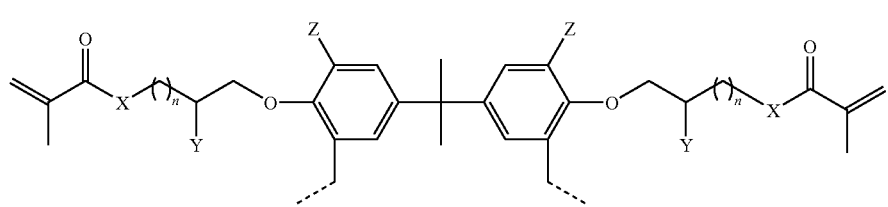
R10
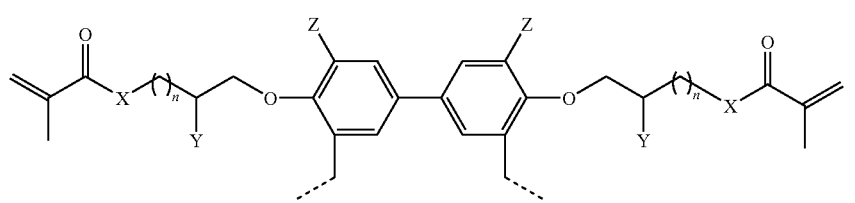
R11
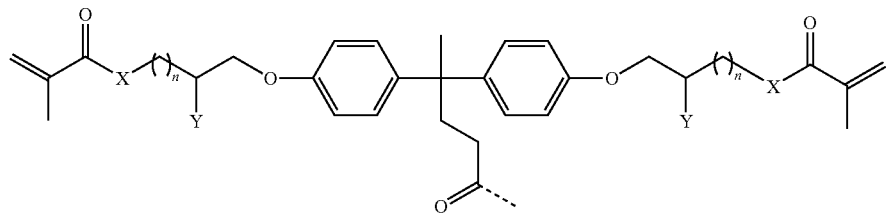

-continued

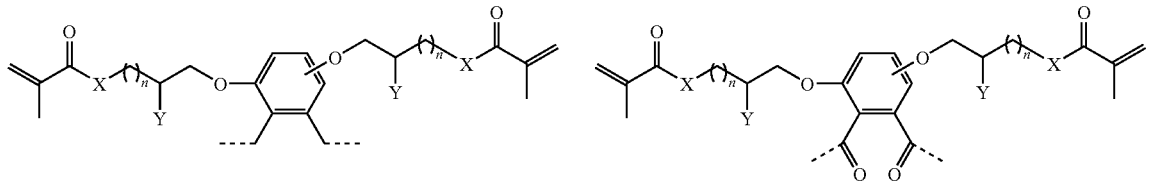

wherein a dotted line represents the bond between R and a chelating group L; X is an ether oxygen or an NH group; Z is hydrogen or a substituted or unsubstituted alkyl group having from 1 to 12 carbon atoms such as methyl, ethyl, propyl, isopropyl, n-butyl, or t-butyl; Y is a pendent group that may or may not participate in chelate formation. The simplest Y is hydrogen, which does not ordinarily participate in chelate formation; and a typical Y is a hydroxyl group, which can participate in chelation. Y may also be, for example, an ester of a phosphoric acid, or a half ester of an aliphatic or aromatic diacid or triacid having from 2 to 12 carbon atoms, such as oxalic acid, malonic acid, maleic acid, a mono- or disubstituted maleic acid, malic acid, succinic acid, fumaric acid, malic acid, tartaric acid, glutaric acid, glutaconic acid, citric acid, adipic acid, pimelic acid, cyclohexen-1,2 diacid, (o, m, or p)-phthalic acid, hydroxyphthalic acid, suberic acid, trimellitic acid, or sebaric acid. The chain length of such a diacid or triacid may be varied to enhance formation of the fluoride-exchange metal chelate, and the release of fluoride from the chelate. The various X groups depicted in the above structures may be the same as, or different from one another, as may the various Y or Z groups. The number n is an integer from 0 to 16. The preferred n is 6 to 12 in R1 to R3 and the preferred n is 0 to 4 in R4 through R13.

Preferred multidentate chelating groups L are those containing bis(carboxymethyl)-L-lysine, hydroxypyridinones, catechols, or substituted or unsubstituted aromatic β-diketones; and having a molecular weight between 100 and 2000, for example, one of the following structures L1-L17:

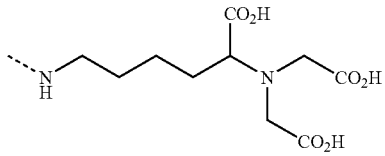

L1

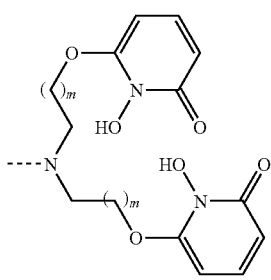

L2

-continued

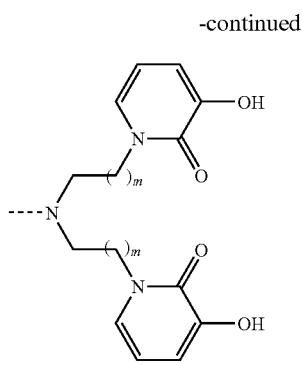

L3

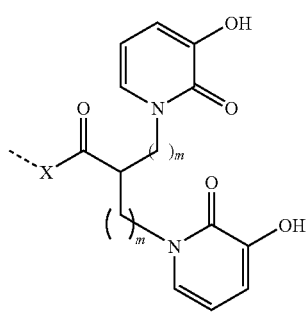

L4

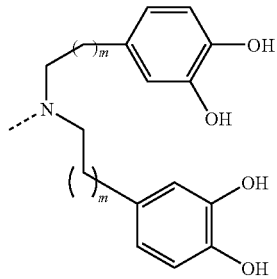

L5

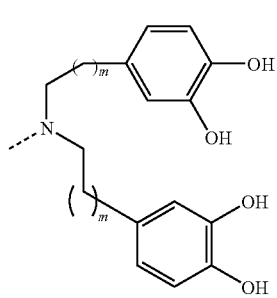

L6

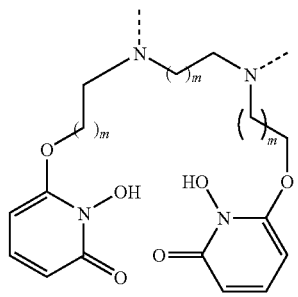

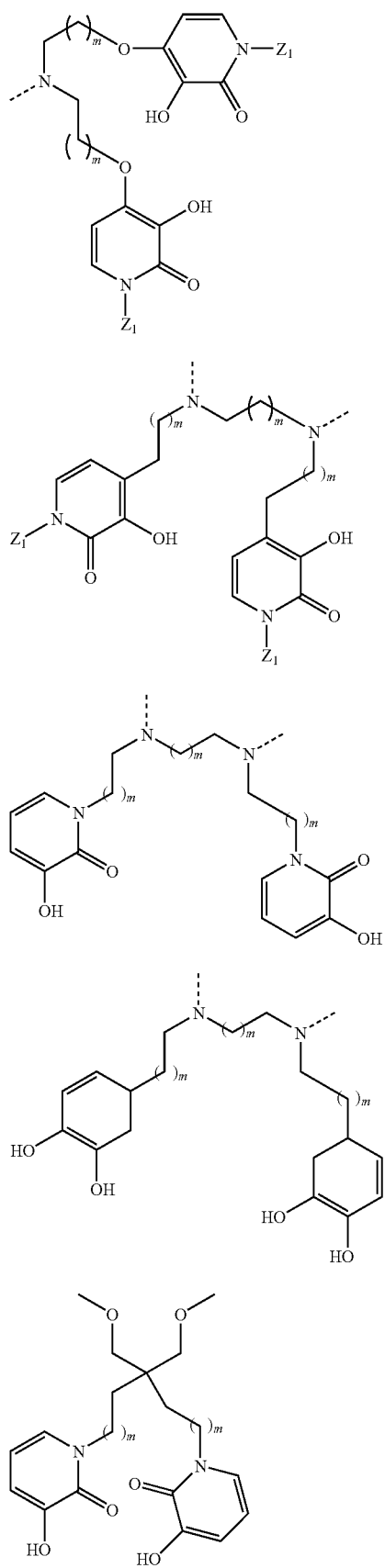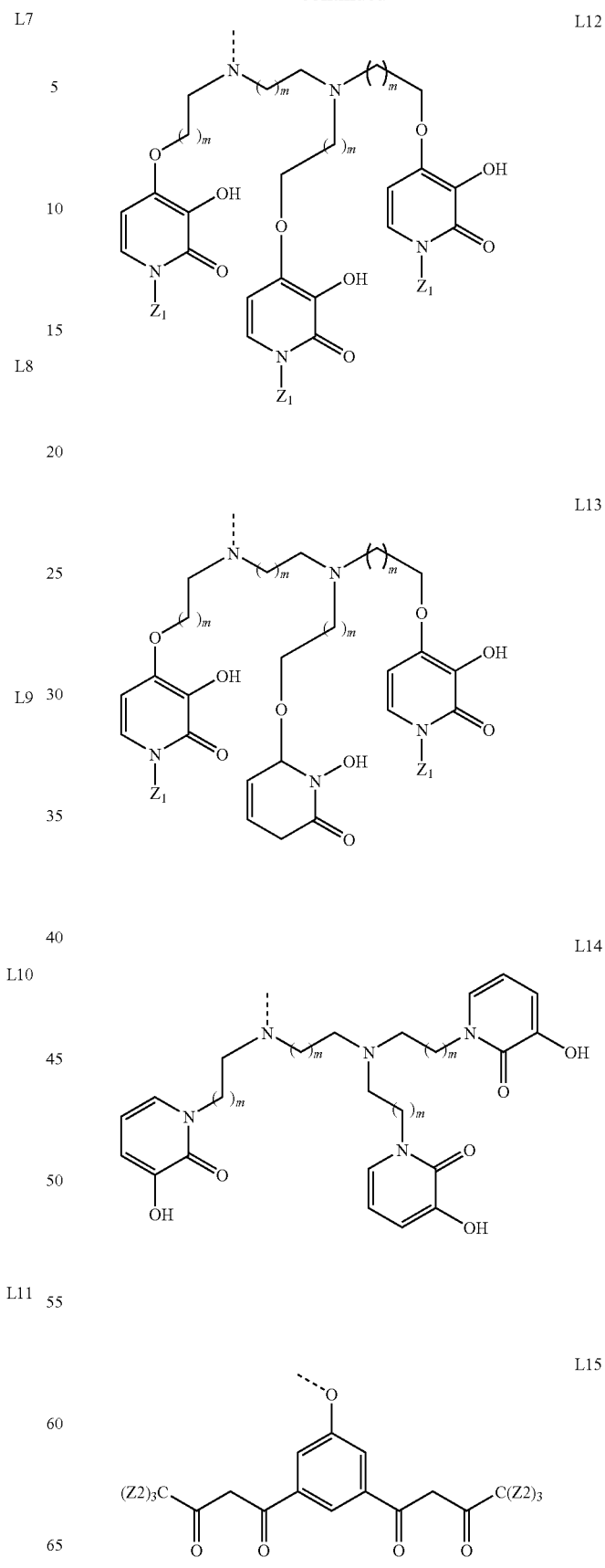

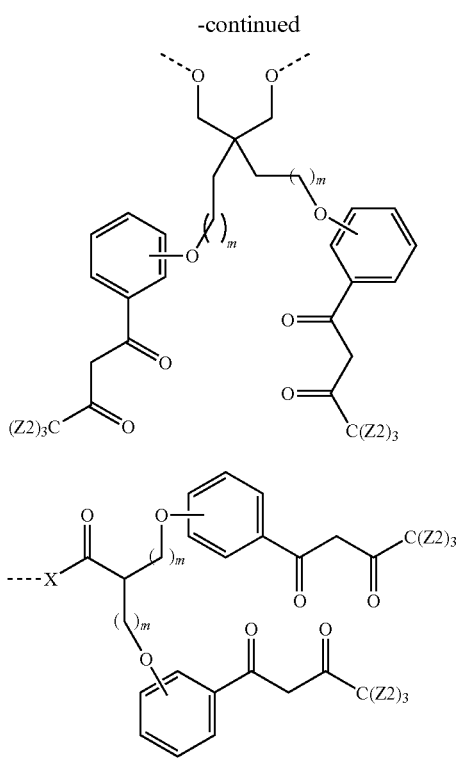

wherein a dotted line represents the bond between R and a chelating group L; X is either an oxygen or an NH group; $Z_1$ is hydrogen or an alkyl group containing 1 to 4 carbons (e.g., methyl, ethyl, propyl, isopropyl, n-butyl, tert-butyl); Z2 is hydrogen, fluorine, or an alkyl group containing 1 to 4 carbons (e.g., methyl, ethyl, propyl, isopropyl, n-butyl, tert-butyl); a preferred Z2 is fluorine; m is an integer from 0 to 6; a preferred m is 0 or 1.

The synthesis of the R and L groups can be carried out separately or in coordination. The R and L groups can be linked (coupled) through ester, amide, ether, amine, or other covalent bonds; formed, for example, by reactions between activated acid and alcohol or amine, between alkyl bromide (or chloride or iodide) and alcohol, or between alkyl bromide (or iodide) and primary or secondary amine. Before the coupling reaction, the "donor" groups on the chelating ligands, such as the —OH or —NOH groups in catechols or hydroxypyridinones, should be protected, for example by forming a methyl or benzyl ether to inhibit unwanted addition reactions to these groups. After the coupling reaction, the protection groups are removed, for example by reaction with $BBr_3$ (to remove a methyl group), or with $H_2/Pd$ or concentrated acid or $BCl_3$ (to remove a benzyl group).

Below are illustrative examples of methods that may be used for the synthesis of the R groups, and linking them to the L groups:

(1) R1 can be synthesized by reaction of methacryloyl chloride with an aliphatic bromo-1-alcohol containing 2-12 carbons, such as bromoethanol, 3-bromo-1-propanol, 4-bromo-1-butanol, 6-bromo-1-hexanol, 8-bromo-1-octanol, 10-bromo-1decanol, 11-bromo-1-undecanol, or 12-bromo-1-dodecanol.

(2) R2 can be synthesized by reaction of methacryloyl chloride with a hydroxyl aliphatic carboxylic acid containing 8-16 carbons, such as 10-hydroxydecanoic acid, 11-hydroxyundecanoic acid, 12-hydroxyoctadecanoic acid, 15-hydroxypentadecanoic acid, 16-hydroxyhexadecanoic acid, or a long chain aliphatic amino acid containing 8-16 carbons such as 11-aminoundecanoic acid, or 12-aminododecanoic acid. Then the acid may be activated by reaction with thionyl dichloride ($SOCl_2$), oxylyl chloride ($COCl_2$), tosyl chloride, dicyclohexylcarbodiimide (DCC) and N-hydroxysuccinimide (NHS), or 2-mercaptothiazoline.

(3) R3 can be synthesized by reaction of methacryloyl chloride with a p-, m-, or o-hydroxybenzoic acid or with a p-, m-, or o-aminobenzoic acids, followed by activation as described above.

(4) R4 and R5 can be synthesized by the reaction of benzene-1,3,5-tricarbonyl trichloride with hydroxyl methacrylate (synthesized with methacryloyl chloride and aliphatic diols such as 2-hydroxyethyl methacrylate (HEMA)), amino methacrylamide (synthesized with methacryloyl chloride and aliphatic diamine), or an amino methacrylate such as 2-aminoethyl methacrylate; and then activating the remaining acid group.

(5) R6 and R7 can be synthesized by reaction of cyclohexane-1,3,5-tricarbonyl trichloride with hydroxyl methacrylate (synthesized with methacryloyl chloride and aliphatic diols such as 2-hydroxyethyl methacrylate (HEMA)), amino methacrylamide (synthesized with methacryloyl chloride and aliphatic diamine), or an amino methacrylate such as 2-aminoethyl methacrylate; and then activating the remaining acid group.

(6) R8 can be synthesized by reaction of phthalic dianhydride with hydroxyl methacrylate (synthesized with methacryloyl chloride and aliphatic diols such as 2-hydroxyethyl methacrylate (HEMA)), amino methacrylamide (synthesized with methacryloyl chloride and aliphatic diamine), or an amino methacrylate such as 2-aminoethyl methacrylate; and then activating the remaining acid group.

(7) R9, R10, and R12 can be synthesized by first coupling protected L groups containing a secondary amine to a substituted or unsubstituted bisphenol, a substituted or unsubstituted biphenol, or dihydroxybenzene, through a Manich-type reaction with formaldehyde, and then reacting with glycidyl methacrylate or glycidyl methacrylamide, and afterwards removing the protective groups.

(8) R11 can be synthesized by first reacting 4,4-bis(4-hydroxyphenyl)pentanoic acid with glycidyl methacrylate, or glycidyl methacrylamide, or 2-bromoethyl methacrylate, or other n-bromoalkyl methacrylate (e.g., synthesized by reaction of n-bromoalcohol and methacryloyl chloride); and then activating the acid group.

(9) R13 can be synthesized by first reacting dihydroxy phthalic acid with glycidyl methacrylate or glycidyl methacrylamide, or reacting dichlorophthalic acid with n-hydroxyalkyl methacrylate or n-hydroxyalkyl methacrylamide; and then activating the acid groups.

Below are illustrative examples of methods that may be used for the synthesis of the ligand groups L:

(1) L1 is bis(carboxymethyl)-L-lysine, which is commercially available.

(2) L2 and L6 can be synthesized by first reacting 2,6-dibromopyridine with dihydroxyalkylamine (whose secondary amine has been linked to an R group), or n-bromoalcohol, and then reacting with a diamine. The bromopyridine groups are then oxidized with $H_2O_2$ to 1,2-HOPO.

(3) L3, L9 and L14 can be synthesized by first reacting 3-methoxypyridin-2(1H-one or 3-benzoxypyridin-2 (1H)-one with a diiodoalkane or a dichloroalkane containing 1 to 5 carbons, or with an n-iodoalcohol containing 1 to 5 carbons; followed by chlorination with tosyl chloride; and then reacting with ammonia or primary amine to form L3, or diamine to form L9 and L13.

(4) L4 can be synthesized by first reacting 3-methoxypyridin-2(1H)-one or 3-benzoxypyridin-2(1H)-one with a dibromo-aliphatic acid such as 3-bromo-2-(bromomethyl)propanoic acid.

(5) L5 can be synthesized by first converting the primary amine group in dopamine to a bromide, by reacting with $NaNO_2$ and HBr, or with a Grignard reagent, and then reacting the bromide with dopamine.

(6) L7, L8, L12, and L13 can be synthesized by first reacting 3-methoxypyridin-2(1H)-one or 3-benzoxypyridin-2(1H)-one with an iodoalkane containing 1 to 5 carbons to form an N-alkyl-substituted pyridinone, and then reacting with $AlCl_3$ or $Br_2$ to form 4-chloro-pyridinone or 4-bromo-pyridinone, which in turn reacts with a dihydroxyl alkylamine (whose secondary amine has been linked to the an R group) to form L7, or with an N-bromoalcohol; the products react with a diamine to form L8 and L12. L13 can be synthesized by addition of the intermediate for the synthesis of L2 and L6 to L8.

(7) L10 can be synthesized by reaction of dopamine with a dibromoalkane or diiodoalkane.

(8) L11 can be synthesized by reaction of 3-methoxypyridin-2(1H)-one or 3-benzoxypyridin-2(1H)-one with a bis(bromoalkyl)-diol such as 2,2-bis(bromomethyl)propane-1,3-diol.

(9) L15 can be synthesized by reaction of dimethyl 5-hydroxyisophthalate with acetone or a substituted acetone such as 1,1,1-trifluoroacetone.

(10) L16 and L17 can be synthesized by first reacting methyl 4-hydroxybenzoate with acetone or a substituted acetone such as 1,1,1-trifluoroacetone, and then reacting with a bis(bromoalkyl)-diol such as 2,2-bis(bromomethyl)propane-1,3-diol, or a dibromo-aliphatic acid such as 3-bromo-2-(bromomethyl)propanoic acid.

The preferred fluoride-releasing monomers may be prepared from chelating monomers such as those described above and metal fluorides or anionic fluoride complexes (as acids or alkyl ammonium salts, e.g. $H_2ZrF_6$ or $(Bu_4N)_2ZrF_6$) that are at least somewhat soluble in a polar organic solvent such as methanol, DMF, tetraethyleneglycol dimethacrylate, dimethylsulfone (DMSO), or a mixed water-organic solvent. The acidic ternary metal fluoride complexes can be converted to the neutral salts of lithium, sodium, tetraalkyl ammonium or pyridinium by reaction with the corresponding hydroxides.

An alternative method for preparing the fluoride-releasing monomers is to first react an acidic chelating monomer with a metal salt that is partially soluble in the organic solvent, e.g., a nitrate or acetate, and then adding fluoride, e.g., as HF, NaF, $NH_4F$, LiF, or a tetraalkyl ammonium fluoride such as $(CH_3)_4NF$, $(C_2H_5)_4NF$, or $[CH_3(CH_2)_3]_4NF$. However, the metal ions may also form strong chelates with multiple chelating monomers or even with polymers that are insoluble in organic or aqueous solvents.

Chelating monomers may be generated from combinations of different polymerizable groups (e.g., R1-R13). Furthermore, the chelating groups may generate many chelating monomers. Examples of such fluoride-releasing monomers formed from chelating monomers, zirconium, and fluoride include the following:

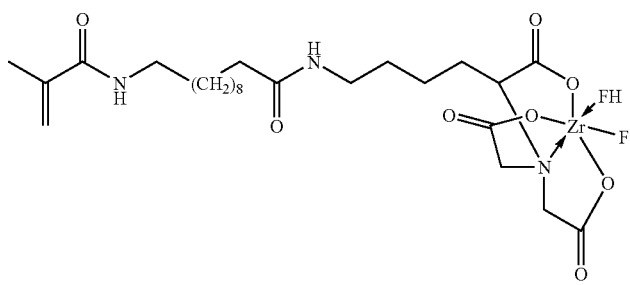

R1L1-ZrF$_2$H

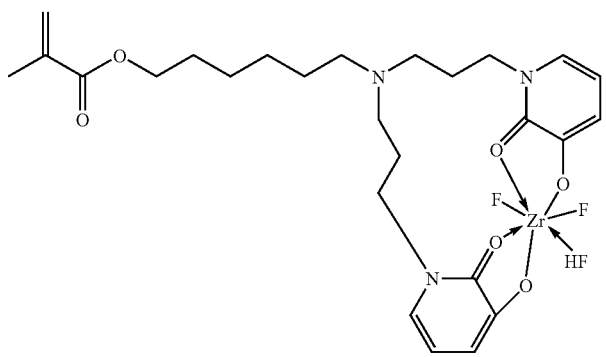

R1L3-ZrF$_3$H

-continued
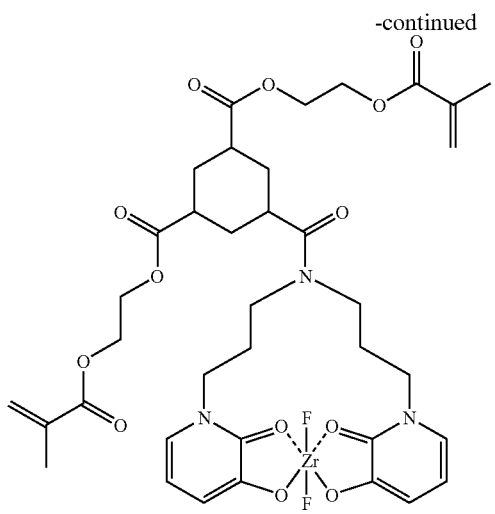
R6L3-ZrF2
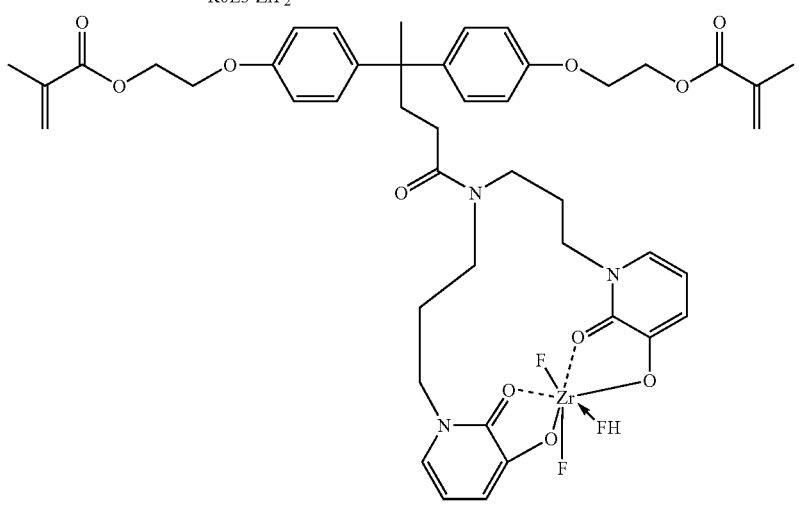
R11L3-ZrF3H
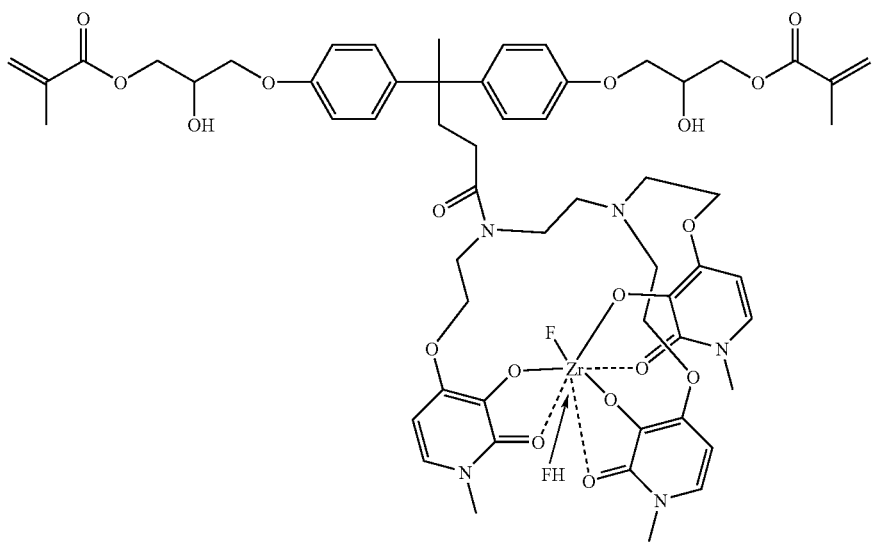
R11L12-ZrF2H

The chelating monomers and fluoride-releasing monomers may be dissolved in, or mixed with, monomers or mixtures of monomers or other materials known in the art for use in dental materials, such as bisphenol A glycidyl dimethacrylate, hydroxylethyl methacrylate, triethyleneglycol dimethacrylate, and urethane dimethacrylate. The amount of the fluoride-releasing monomers may be from about 0.1% to about 70% by weight of total monomers, depending on the requirements for fluoride release and other physical and mechanical properties, the preferred ratio being from about 20% to about 40%. The monomer mixtures may be polymerized (cured) by means known in the art, such as free radical reactions initiated by photoinitiators or chemical initiators. Such photoinitiators include diketones such as camphorquinone, and 1-phenyl-1, 2-propanedione (PPD). Preferred chemical initiators are organic peroxides such as benzoyl peroxide. Reducing agents or accelerators may also be added, such as aliphatic or aromatic tertiary amines, for example dimethylaminoethyl methacrylate. The total ratio of initiators and accelerators is typically between about 0.03% and about 5% by weight of total materials, with a preferred range between about 0.3% and about 1%.

The chelating monomers containing ligand group L1, fluoride-releasing monomers and their mixtures can be used in self-etching primers and self-etching dental bonding agents. Their concentration may be from 1% to about 50% by weight of total solution. The self-etching primers and dental bonding agents may contain other dental monomers, photoinitiators and solvents.

The chelating monomer, fluoride-releasing monomers and their mixtures with other monomers may be used with or without fillers. Preferred compositions for dental composite resins contain both fluoride-releasing monomers and fluoride-releasing filler particles such as a fluoroaluminosilicate glass, for example, that described in U.S. Pat. No. 5,332,429. The fillers may also include other inorganic compounds such as $SiO_2$, $ZrO_2$, $TiO_2$, $ZrF_4$, NaF, $AlF_3$, LiF, $SrF_2$, $CeF_3$, $Ca_3(PO_4)_2$, $La_2O_3$, $Ce_2O_3$ and glasses incorporating these compounds. Preferred particle sizes for fillers are 0.1 to 5 micrometer, more preferably 0.2 to 3 micrometer.

To enhance bonding between the filler and the resin matrix, the filler surface is preferably treated with a silane coupling agent, such as γ-methacryloyl-oxypropyltrimethoxysilane, γ-mercaptopropyltriethoxysilane, γ-aminopropyltrimethoxysilane, or O-(methacryloxyethyl)-N-(triethoxysilylpropyl) urethane. Alternatively, the filler particles may be treated with an organic acid containing one or more polymerizable functional groups, including for example one or more chelating monomers in accordance with the present invention. The filler load may vary by type of application: for example, it can range from about 5% to about 50% in a sealant or a filled dental adhesive, from about 40% to about 60% for flowable composites, and up to about 85% for posterior composites.

Applications for the chelating monomers and fluoride-releasing monomers of the present invention include, for example, dental restorative materials such as composite resins, compomers, resin-modified glass ionomers, sealant, liners, cements, provisional/temporary materials, dental adhesives (bonding agents), denture base resins, and orthodontic adhesives.

Alternatively, polymers and composites made from the novel chelating monomers and their metal chelates may also be used in the preparation of ion exchange resins, which may be used, for example, in the separation of metals, fluoride ions, and other anions by chemical manufacturers or analytical laboratories; or in the removal of hazardous metals or unwanted fluoride from industrial waste water. The chelating monomers may also be used to coat metal surfaces including dental and medical implants to enhance protection or bonding.

Examples are given below of several of the synthesis of several embodiments of chelating monomers in accordance with this invention, namely, certain ternary zirconium fluoride chelates and their use in fluoride-releasing dental bonding agents.

Reagents and Analyses. Methacryloyl chloride, 10-aminodecanoic acid, N-hydroxysuccinimide (NHS), dicyclohexylcarbodiimide (DCC), $N_\alpha,N_\alpha$-bis(carboxymethyl)-L-lysine, $H_2ZrF_6$ (48% solution in $H_2O$), camphorquinone (CQ), 2-(dimethylamino)ethyl methacrylate (DMAEM), phenyl bis (2,4,6-trimethylbenzoyl)phosphine oxide (PO), dimethylformamide (DMF), hydrochloric acid (HCl, 37%), acetic acid, sodium carbonate, tetrahydrofuran (THF), diethyl ether, anhydrous magnesium sulfate ($MgSO_4$), and ethyl acetate were used as received from Aldrich. Fourier transform infrared (FTIR) spectra were recorded on a Bio-Rad FTS-40 FTIR spectrometer. NMR spectra were measured by a Bruker AC400 NMR spectrometer, using $CDCl_3$, $CD_3OD$ or DMSO-$d_6$ as solvent. ESMS was carried out on a Bruker Daltonic Esquire 3000 Ion Trap mass spectrometer. The sample solutions (approx. $10^{-4}$ M) were directly infused via a syringe pump (model 74900, ColeParmer) at a flow rate of 240 µl/h. The non-fluoride-releasing commercial dental composite Synergy Flow™ and its resin components (activated, unfilled monomer 12166-KG13™, and silanized filler 12204-JE39™) were provided by Coltene Whaledent (Mahwah, N.J.). Fluoride-releasing flowable composites were obtained from Ivoclar Vivadent (Tetric-Flow™) and Pulpdent (Flows-Rite™). Commercial bonding agents Clearfil SE Bond™ and Clearfil Protect Bond™ were provided by Kurarary.

EXAMPLE 1

Synthesis of 11-Methacrylamidoundecanoic Acid

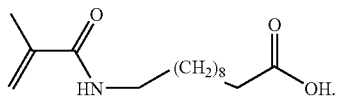

10-Aminodecanoic acid (4.04 g, 20 mmol) was dissolved in 300 ml of THF and water (1:1) in an ice-water bath, and then sodium carbonate (3.18 g, 30 mmol) was added. Methacryloyl chloride (3.15 g, 30 mmol) was slowly added, and the mixture was stirred for 5 h. After reaction was complete, the solution was neutralized to pH 5 with HCl. Then the solvent was removed by evaporation, and the residue was extracted with 200 ml $CH_2Cl_2$, producing a white solid. Recrystallization from a hexane/ethyl acetate solution gave 4.96 g product (yield 92%). Alternatively, replacing THF/$H_2O$ with $CHCl_3$ gave a similar or higher yield.

Analysis: $^1$HNMR ($CDCl_3$, 400 MHz) δ: 5.69 (s, 1H, CHH=), 5.32 (s, 1H, CHH=), 3.30 (m, 2H, $NHCH_2CH_2$), 2.34 (t, 2H, J=7.4 Hz, $CH_2CH_2COOH$), 1.97 (s, 3H, $CH_2$=CH$CH_3$), 1.48-1.70 (m, 4H, $NHCH_2CH_2CH_2$ and $CH_2CH_2CH_2COOH$), 1.24-1.38 (m, 12H, $NHCH_2CH_2$($CH_2$)$_6$ $CH_2CH_2COOH$). $^{13}$C-NMR ($CDCl_3$, 400 MHz) δ: 179.50 (COOH), 168.86 ($CH_2$=$CCH_3CONHCH_2$), 140.26 ($CH_2$=$CCH_3CONHCH_2$), 119.67 ($CH_2$=$CCH_3$), 40.00 ($CH_2$=$CCH_3CONHCH_2CH_2$), 34.29 ($CH_2CH_2COOH$), 29.70, 29.57, 29.47, 29.40, 29.35, 29.19, 27.10, 24.90

($CH_2$=$CCH_3CONHCH_2(CH_2)_8CH_2COOH$), 18.92 ($CH_2$=$CCH_3$). ESMS (THF/$H_2O$, negative ion): m/z=268.2 ([M−H]⁻, calculated: 268.2).

EXAMPLE 2

Synthesis of 2,5-Dioxopyrrolidin-1-yl-11-Methacrylamidoundecanoate (Compound 2)

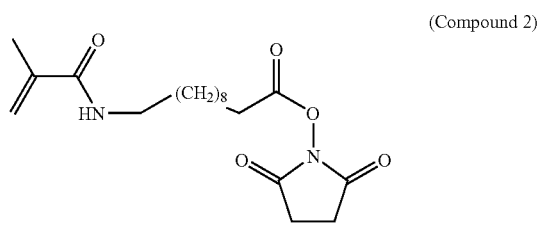

(Compound 2)

To a solution of 11-methacrylamidoundecanoic acid (1.35 g, 5 mmol) in ethyl acetate/dimethylformamide (50 ml, 1:1) in ice/water bath were added solutions of N-hydroxysuccinimide (0.58 g, 5 mmol) and of dicyclohexylcarbodiimide (DCC, 1.03 g, 5 mmol), each in dimethylformamide (10 ml). The resulting mixture was stirred for 2 h in an ice/water bath, and then stirred at room temperature overnight in darkness. Glacial acetic acid (0.05 ml) was then added. After stirring for 1 h, the solution was filtered, and the solvents were removed, giving the crude product. Recrystallization from an ethanol solution gave 1.32 g product (yield 72%).

Analysis: $^1$H NMR ($CD_3OD$, 400 MHz) δ: 5.66 (s, 1H, CHH=), 5.35 (s, 1H, CHH=), 3.22 (m, 2H, $NHCH_2CH_2$), 2.63 (t, 4H, J=6.6 Hz, $COCH_2CH_2CO$), 2.53 (t, 2H, J=6.8 Hz, $CH_2CH_2COO$), 1.93 (s, 3H, $CH_2$=$CHCH_3$), 1.48-1.74 (m, 4H, $NHCH_2CH_2$ and $CH_2CH_2COO$), 1.28-1.38 (m, 12H, $NHCH_2CH_2(CH_2)_6CH_2CH_2COO$). $^{13}$C NMR ($CD_3OD$, 400 MHz) δ: 171.86 ($COCH_2CH_2CO$), 171.17 ($CH_2$=$CCH_3CONHCH_2$), 170.27 ($CH_2COO$), 141.47 ($CH_2$=$CCH_3CONHCH_2$), 120.16 ($CH_2$=$CCH_3$), 40.66 ($CH_2$=$CCH_3CONHCH_2CH_2$), 32.17 ($CH_2CH_2COO$), 30.58, 30.48, 30.41, 30.29, 30.00, 29.77, 28.02, 26.49 ($CH_2$=$CCH_3CONHCH_2(CH_2)_8CH_2COO$), 25.76 ($COCH_2CH_2CO$), 18.87 ($CH_2$=$CCH_3$).

EXAMPLE 3

Synthesis of chelating monomer R1L1, 2,2'-(1-Carboxy-5-(11-methacrylamidoundecanamido)pentylazanediyl)diacetic acid, (Compound 3)

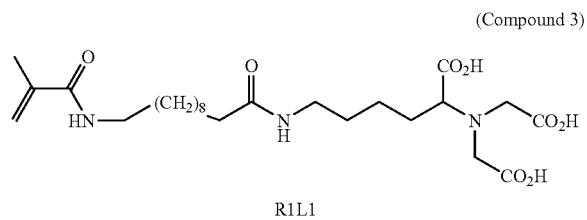

(Compound 3)

R1L1

To $N_\alpha,N_\alpha$-bis(carboxymethyl)-L-lysine (262.1 mg, 1 mmol) in water (10 ml) in an ice/water bath was added 2,5-dioxocyclopentyl-1'-methacrylamidoundecanoate (336.2 mg, 1 mmol) in 10 ml THF and $Na_2CO_3$ (106 mg, 1 mmol). The resulting mixture was stirred for 2 h in an ice/water bath, and then stirred at room temperature overnight in darkness. After reaction was complete, the solution was acidified to pH 2. Then the solvent was removed by evaporation, and the residue was extracted with THF. Recrystallization of the crude product from a chloroform/ether solution gave 328.4 mg product (yield 64%).

Analysis: $^1$H NMR (DMSO-$d_6$, 400 MHz) δ: 5.62 (s, 1H, CHH=), 5.29 (s, 1H, CHH=), 3.47 (s, 4H, $NH(CH_2)_2CH_2CH_2CH(COOH)N(CH_2COOH)_2$), 3.32 (t, 1H, J=7.4 Hz, $NHCH_2(CH_2)_3CH(COOH)N(CH_2COOH)_2$), 3.08 (m, 2H, $NHCH_2(CH_2)_3CH(COOH)N(CH_2COOH)_2$), 2.99 (m, 2H, $NHCH_2(CH_2)_9CONH$), 2.02 (t, 2H, J=7.4 Hz, $NH(CH_2)_9CH_2CONH$), 1.84 (s, 3H, $CH_2$=$CHCH_3$), 1.31-1.66 (m, 8H, $NHCH_2CH_2(CH_2)_8CH_2CH_2CONH$ and $NHCH_2CH_2CH_2CH_2CH(COOH)N(CH_2COOH)_2$)), 1.18-1.30 (m, 14H, $NH(CH_2)_2(CH_2)_6(CH_2)_2CONH$ and $NH(CH_2)_2CH_2CH_2CH(COOH)N(CH_2COOH)_2$). $^{13}$C NMR (DMSO-$d_6$, 400 MHz) δ: 173.92 ($NH(CH_2)_4CH(COOH)N(CH_2COOH)_2$), 173.19 ($NH(CH_2)_4CH(COOH)N(CH_2COOH)_2$), 171.79 ($NH(CH_2)_9CH_2CONH$), 167.21 ($CH_2$=$CCH_3CONH(CH_2)_9CH_2CONH$), 140.03 ($CH_2$=$CCH_3CONH(CH_2)_9CH_2CONH$), 118.54 ($CH_2$=$CCH_3CONH(CH_2)_9CH_2CONH$), 64.19 ($NH(CH_2)_4CH(COOH)N(CH_2COOH)_2$), 53.28 ($NH(CH_2)_4CH(COOH)N(CH_2COOH)_2$), 38.75, ($CH_2$=$CCH_3CONHCH_2(CH_2)_9CONH$), 38.13 ($NHCH_2(CH_2)_3CH(COOH)N(CH_2COOH)_2$), 35.33 ($CH_2$=$CCH_3CONH(CH_2)_9CH_2CONH$), 29.23, 28.97, 28.89, 28.82, 28.78, 28.70, 28.68, 28.62, 26.36, 25.23, 23.02 ($CH_2$=$CCH_3CONHCH_2(CH_2)_8CH_2COOH$ and $NHCH_2(CH_2)_3CH(COOH)N(CH_2COOH)_2$). ESMS (THF/$H_2O$, negative ion): m/z=512.3 ([M−H]⁻, calculated: 512.2).

EXAMPLE 4

Synthesis of 2,2'-(1-Carboxy-5-(11-methacrylamidoundecanamido)pentylazanediyl)diacetic acid zirconium (IV) fluoride complex (Compound 4)

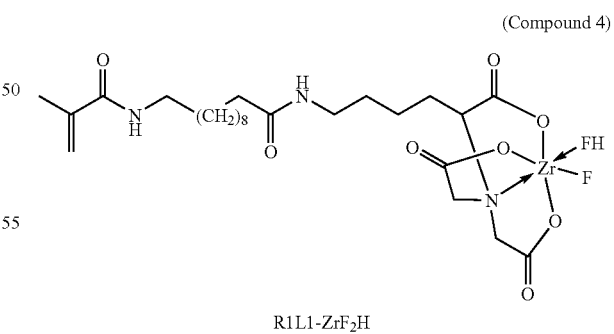

(Compound 4)

R1L1-ZrF₂H

To a solution of 2,2'-(1-carboxy-5-(11-methacrylamidoundecanamido)pentylazanediyl)diacetic acid (51.3 mg, 0.1 mmol) in 10 ml THF and water (1:1) was slowly added $H_2ZrF_6$ (43.1 mg, 0.1 mmol, 48% solution in $H_2O$) with stirring at room temperature. After 1 h, the mixture was filtered. A colorless oil complex was obtained, 70 mg (97.2% yield) after removal of the solvents. ESMS (THF/H$_2$O, negative ion): m/z=638.2 ([M−H]$^-$, calculated: 638.2).

EXAMPLE 5

Synthesis of 2,2'-(1-Carboxy-5-(11-methacrylamidoundecanamido)pentylazanediyl)diacetic Acid Zirconium (IV) Fluoride Complex (Compound 5)

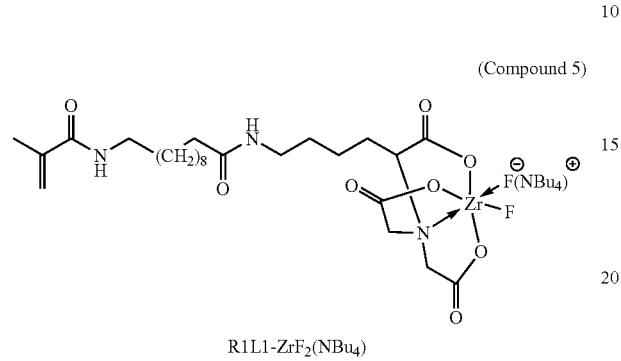

(Compound 5)

R1L1-ZrF$_2$(NBu$_4$)

To a solution of ZrF$_4$ (16.7 mg, 0.1 mmol) in 10 ml THF and water (1:1) was added (C$_4$H$_9$)$_4$NF (28.1 mg, 0.1 mmol) with stirring at room temperature. After 1 h, 2,2'-(1-carboxy-5-(11-methacrylamidoundecanamido)pentylazanediyl)diacetic acid (51.3 mg, 0.1 mmol), in 10 ml THF and water (1:1), was slowly added to the solution with stirring at room temperature. After 1 h, the mixture was filtered. Colorless oil complex (Compound 5) was obtained (90 mg, 93.7%) after the solvents were removed. ESMS (THF/H$_2$O, negative ion): m/z=638.0 ([M−NBu$_4$]$^-$, calculated: 638.1). ESMS positive ion: m/z=242.4 ([NBu$_4$]$^+$, calculated: 242.28)

EXAMPLE 6

Synthesis of 3-(benzyloxy)pyridin-2(1H)-one (6)

Compound 6

KOH (10 g, 180 mmol) was stirred in methanol (260 mL) for 10 minutes, until completely dissolved. Then 2,3-dihydroxypyridone (20 g, 180 mmol) was added to the KOH/methanol solution, which was then stirred for another 10 minutes. Benzyl chloride (23.6 mL, 200 mmol) was then slowly added to the reaction mixture. The reaction mixture was stirred and heated at 40° C. Reaction progress was monitored by ESMS. After 3.5 hours, ESMS showed that the starting material 2,3-dihydroxypyridinone had been almost completely consumed. Then the methanol solvent was evaporated under vacuum at 40° C. The residue was dissolved with water (100 mL) and extracted 3 times (150 mL) with CH$_2$Cl$_2$. The combined organic extracts were dried over MgSO$_4$, filtered, and concentrated in vacuo. Recrystallization in ethanol gave 10.14 g (28% yield) of product 3-(benzyloxy)pyridin-2(1H)-one (Compound 6). ES-MS (positive ion in MeOH/H$_2$O): m/z=202.1, ([M+H]$^+$ calculated: 202.09).

EXAMPLE 7

Synthesis of 3-(benzyloxy)-1-(3-iodopropyl)pyridin-2(1H)-one (Compound 7)

Compound 7

To a solution of 1,3-diiodopropane (7.1 mL, 63 mmol) in tetrahydrofuran (50 mL) was added 3-(benzyloxy)pyridin-2(1H)-one (1.28 g, 6.3 mmol) and Na$_2$CO$_3$ (0.67 g, 6.3 mmol). The mixture was then stirred at 70° C. for 1 day. Reaction progress was monitored by ES-MS. After ESMS showed essentially complete consumption of the starting material 3-(benzyloxy)pyridin-2(1H)-one, the reaction was stopped. Then the reaction mixture was filtered, concentrated, and subjected to flash column chromatography (eluent: hexane:ethylacetate 1:1). Compound 7 was obtained (240 mg, 10% yield). Analysis: ES-MS (positive ion in MeOH/H$_2$O): m/z=370.2, ([M+H]$^+$, calculated: 370.03).

EXAMPLE 8

Synthesis of 1,1'-(3,3'-(6-hydroxyhexylazanediyl)bis(propane-3,1-diyl))bis(3-benzyloxy)pyridin-2(1H)-one) (Compound 8)

Compound 8

To a solution of 6-amino-hexanol (11.7 mg, 0.1 mmol) in tetrahydrofuran (1 mL) was added 3-(benzyloxy)-1-(3-iodopropyl)pyridin-2(1H)-one (74 mg, 0.2 mmol), and Na$_2$CO$_3$ (22 mg, 0.2 mmol). The reaction mixture was then stirred at 70° C. for 1 day. Reaction progress was monitored by ES-MS. After ESMS showed essentially complete consumption of the starting material 3-(benzyloxy)-1-(3-iodopropyl)pyridin-2(1H)-one, the reaction was stopped. Then the reaction mixture was filtered, concentrated, and washed with hexane, yielding Compound 8. Analysis: ES-MS (positive ion in MeOH/H$_2$O): m/z=600.6, ([M+H]$^+$, calculated: 600.34).

EXAMPLE 9

Synthesis of 6-(bis(3-(3-(benzyloxy)-2-oxopyridin-1(2H)-yl)propyl)amino)hexyl methacrylate (Compound 9)

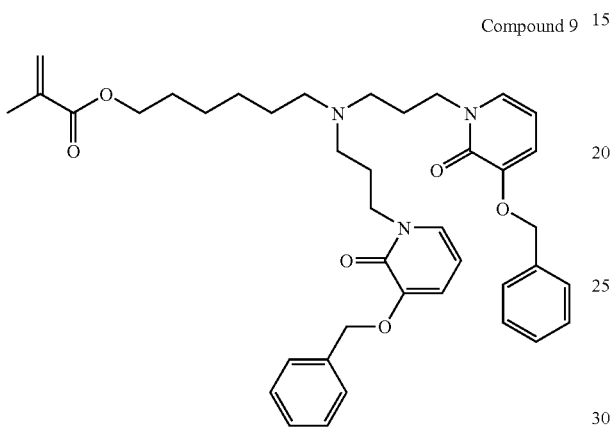

(Compound 9)

To a mixture of 6-(bis(3-(3-(benzyloxy)-2-oxopyridin-1(2H)-yl)propyl)amino)hexyl methacrylate (0.05 mmol) in CH$_2$Cl$_2$ (2 mL) was added methacryloyl chloride (0.06 mmol) at 0° C. The mixture was stirred for 10 minutes under nitrogen, and then triethylamine (6 μL) was added to the mixture with stirring. The temperature of the reaction mixture was gradually increased to room temperature, and the reaction mixture continued to be stirred for 1 day. The reaction progress was monitored by ES-MS. After the reaction had completed, the solvent mixture was removed at 40° C. under vacuum. A solid product was obtained, Compound 9. The product was purified by column chromatography. Analysis: ES-MS (positive ion in MeOH/H$_2$O): m/z=668.7, ([M+H]$^+$, calculated: 668.4).

EXAMPLE 10

Synthesis of chelating monomer R1L3,6-(bis(3-(3-hydroxy-2-oxopyridin-1(2H)-yl)propyl)amino)hexyl methacrylate (Compound 10)

(Compound 10)

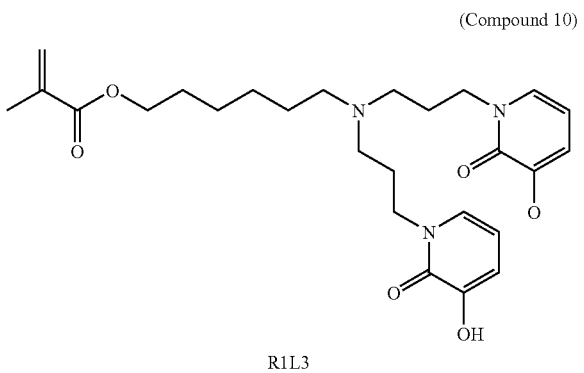

R1L3

To a pre-cooled flask was added a mixture of 6-(bis(3-(3-(benzyloxy)-2-oxopyridin-1(2H)-yl)propyl)amino)hexyl methacrylate (Compound 9) (0.02 mmol) and trichloroboron (1 M in CH$_2$Cl$_2$, 0.1 mL) at 0° C. The mixture was stirred under nitrogen for 2 hours, as the temperature was gradually increased from 0° C. to room temperature. Reaction progress was monitored by ES-MS. After ESMS showed essentially complete consumption of the starting material 6-(bis(3-(3-(benzyloxy)-2-oxopyridin-1(2H)-yl)propyl)amino)hexyl methacrylate, the reaction was stopped. Then methanol (2 mL) was slowly added to the reaction mixture with stirring for 10 minutes to react with the excess trichloroboron. The solvent was then removed at 40° C. under vacuum to give the solid product Compound 10. The product was purified by column chromatography. Analysis: ES-MS (positive ion in MeOH/H$_2$O): m/z=488.5, ([M+H]$^+$, calculated: 488.3).

EXAMPLE 11

Synthesis of 6-{(bis[3-(3-hydroxy-2-oxo-1,2-dihydropyridin-1-yl) propyl]amino}hexyl methacrylate zirconium (IV) fluoride complex (Compound 11)

(Compound 11)

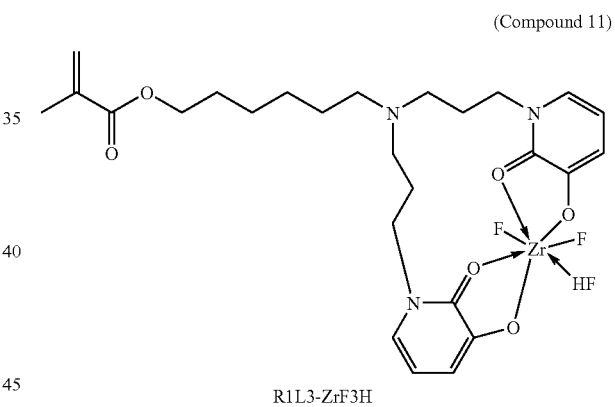

R1L3-ZrF3H

To a solution of Compound 10 (0.01 mmol) in MeOH (0.2 mL) was slowly added H$_2$ZrF$_6$ (4.5 wt % solution in water, 45 μL, 0.01 mmol) with stirring at room temperature. After 30 minutes, the solvent was evaporated, and Compound 11 was obtained as a white solid. ES-MS (negative ion in MeOH/H$_2$O): m/z=632.3, ([M−H]$^-$, calculated: 632.15). The ES-MS spectra at different pH values (4-9) indicated that complex 11 can survive at pH=7.5 (MeOH/H$_2$O, 70/30), which is of clinical importance since normal physiological pH is ~7.2-7.4.

The following examples demonstrate an alternative method to synthesize chelating monomers containing 3,2-HOPO groups. This method offers high yield and easily purified products, with minimal formation of unwanted by-products.

EXAMPLE 12

Synthesis of 3-(benzyloxy)-1-(3-hydroxypropyl)pyridin-2(1H)-one (Compound 12)

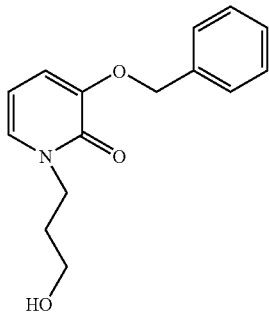

Compound 12

To the solution of Compound 6 (0.202 g, 1 mmol) in acetonitrile was added $K_2CO_3$ (2 equiv.) followed by iodopropanol (0.186 g, 1 mmol). The reaction mixture was stirred at 65° C. overnight. On completion of the reaction, the reaction mixture was filtered and solvent was evaporated under vacuum. The residue was dissolved in water and extracted three times with $CH_2Cl_2$. The combined organic extracts were dried over $Na_2SO_4$, filtered, and concentrated in vacuum. The resulting compound 12 was purified by column chromatography (2:100, $CH_3OH/CH_2Cl_2$). Yield: (85%)

Analysis: $^1$HNMR: δ 1.9 (m, 2H, —N—CH$_2$—CH$_2$—CH$_2$—OH), δ 3.25 (br, 1H, —OH), δ 3.5 (m, 2H, —N—CH$_2$—CH$_2$—CH$_2$—OH) δ 4.19 (m, 2H, —CH$_2$—OH), δ 5.1 (m, 2H, Ph-O—CH$_2$-Ph) δ 6.15 (m, 1H, Ph), δ 6.7 (m, 1H, Ph) δ 6.95 (m, 1H, Ph) δ 7.3-7.5 (m, 5H, Ph). ES-MS (positive ion, in methanol); m/z=260.0 ([M]$^+$, calculated: 260.12).

EXAMPLE 13

Synthesis of 3-(benzyloxy)-1-(3-chloropropyl)pyridin-2(1H)-one (Compound 13)

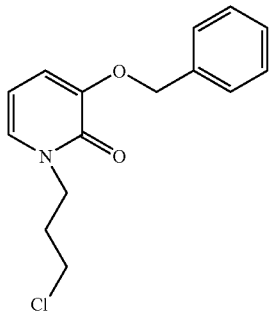

Compound 13

Triethylamine (3 mmol) followed by tosyl chloride (1.25 mmol) were added to a stirred solution of 12 (1 mmol) in dry $CH_2Cl_2$ at room temperature. The reaction mixture was stirred overnight, diluted with $CH_2Cl_2$ (100 ml), and washed with 5% $NaHCO_3$ (3×50 ml) and brine (1×50 ml). The organic solution was dried over $Na_2SO_4$ and concentrated in vacuo. The yellow oil was purified by flash chromatography (cyclohexane:AcOEt 70:30) to give Compound 13 in 86% yield.

Analysis: $^1$H-NMR: δ 2.3 (m, 2H, —N—CH$_2$—CH$_2$—CH$_2$—Cl), δ 3.5 (m, 2H, —N—CH$_2$—CH$_2$—CH$_2$—OH), δ 4.2 (m, 2H, —N—CH$_2$—CH$_2$—CH$_2$—OH), δ 5.1 (m, 2H, Ph-O—CH$_2$-Ph), δ 6.05 (m, 1H, Ph) δ 6.7 (m, 1H, Ph) 6.95 (m, 1H, Ph) δ 7.3-7.5 (m, 5H, Ph). ES-MS (positive ion, in methanol); m/z=278.3 ([M]$^+$, calculated: 278.09).

EXAMPLE 14

Synthesis of 1,1'-(3,3'-azanediylbis(propane-3,1-diyl))bis(3-(benzyloxy)pyridin-2(1H)-one) (Compound 14)

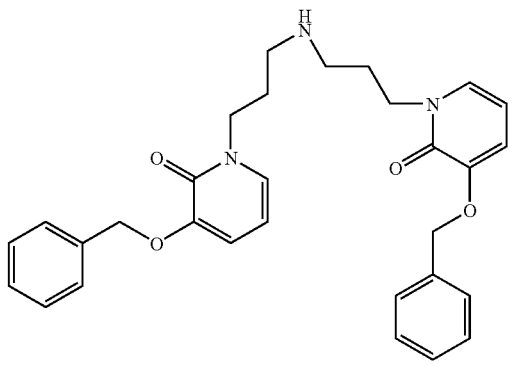

Compound 14

A solution of 7M ammonia in methanol (3.12 mL) was added to 1.0 mmol of compound 13 (dissolved in 2 mL of methanol) in a sealed 10 mL microwavable vial. The reaction mixture was heated with stirring at 130° C. in a MARS microwave reaction system (CEM Corporation) for 2 hours. The solvent was evaporated under vacuum to obtain the product 14. Analysis: ES-MS (positive ion, in methanol); m/z=500.7 ([M+K]$^+$, calculated: 500.25).

EXAMPLE 15

Synthesis of 4,4-bis(4-(2-(methacryloyloxy)ethoxy) phenyl)pentanoic acid (Compound 15)

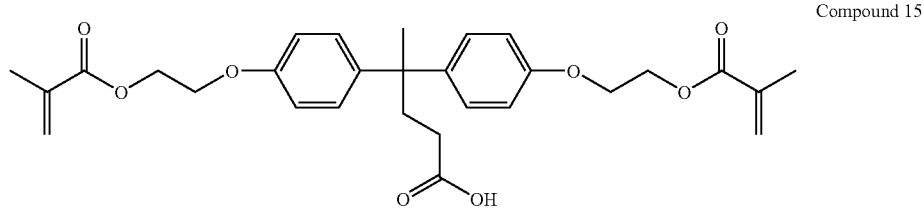

Compound 15

A mixture of compound 4 (1 mmol), $K_2CO_3$ (2 mmol) in 2 ml of acetone was added to a solution of 2-bromomethacrylate (2.2 mmol) in 2 ml acetone. The mixture was stirred with reflux. After the completion of reaction (12 h to 24 h), the acetone solvent was evaporated from the reaction mixture, and the white residue was re-dissolved in methanol. Following evaporation of the methanol, a white solid product remained.

Analysis: $^1$HNMR: δ 1.42 (s, 3H, $(Ph)_2(CH_2)$—C—$CH_3$), δ 1.93 (m, 6H, —OOC—$C(CH_3)$=$CH_2$), δ 1.85-2.00 (m, 2H, $CH_2$—$CH_2$—COOH), δ 2.15-2.25 (m, 2H, $CH_2$—$CH_2$—COOH) δ 4.1-4.2 (m, 4H, Ph-O—$CH_2$—$CH_2$—O—CO), δ 4.2-4.3 (m, 2H, Ph-O—$CH_2$—$CH_2$—O—CO), δ 5.6-5.7 (m, 2H, —C=$CH_2$) δ 5.9-6.0 (m, 2H, —C=$CH_2$) δ 6.5-6.65 (m, 4H, Ph) δ 6.8-6.9 (m, 4H, Ph). ES-MS (positive ion, in methanol); m/z=549.1 ($[M+K]^+$, calculated: 549.19); (negative ion, in methanol); m/z=509.1 ($[M-H]^-$, calculated: 509.23).

EXAMPLE 16

Synthesis of 2,2'-(4,4'-(5-(bis(3-(3-(benzyloxy)-2-oxopyridin-1(2H)-yl)propyl)amino)-5-oxopentane-2,2-diyl)bis(4,1-phenylene))bis(oxy)bis(ethane-2,1-diyl)bis(2-methylacrylate) (Compound 16)

To a stirred suspension of 1-methyl-2-chloropyridiniumiodide (0.613 g, 2.4 mmol) in 1,4-dioxane (10 ml) were added compound 15 (2 mmol) and triethyl amine (0.486 g, 4.8 mmol) at room temperature. After dropwise addition of a solution of compound 14 (2.6 mmol) in 1,4-dioxane (5 ml), the mixture was stirred for about 24 h at 70° C., and was monitored by ESMS. The mixture was filtered, and the 1,4-dioxane solvent was evaporated. The residue was taken up in dichloromethane (50 mL). That solution was washed with 0.5 N aqueous HCL solution, (4×50 mL) and brine (3×50 mL). The collected organic layer was dried over sodium sulfate and evaporated, and the residue was then purified by flash chromatography by elution with dichloromethane: methanol 98:2 (v/v) to give white solid compound 16.

Analysis: ES-MS (positive ion, in methanol): m/z=992.3, ($[M+H]^+$, calculated 992.46).

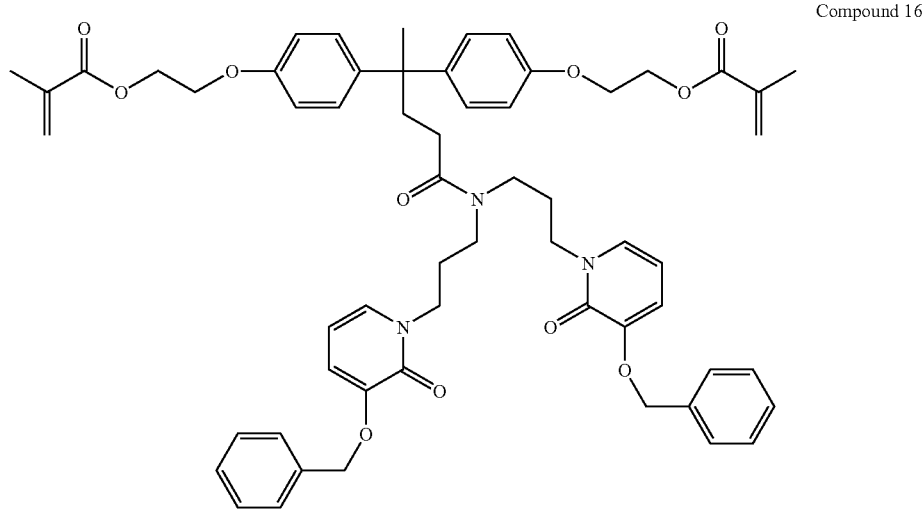

Compound 16

EXAMPLE 17

Synthesis of chelating monomer R11L3 (Compound 17)

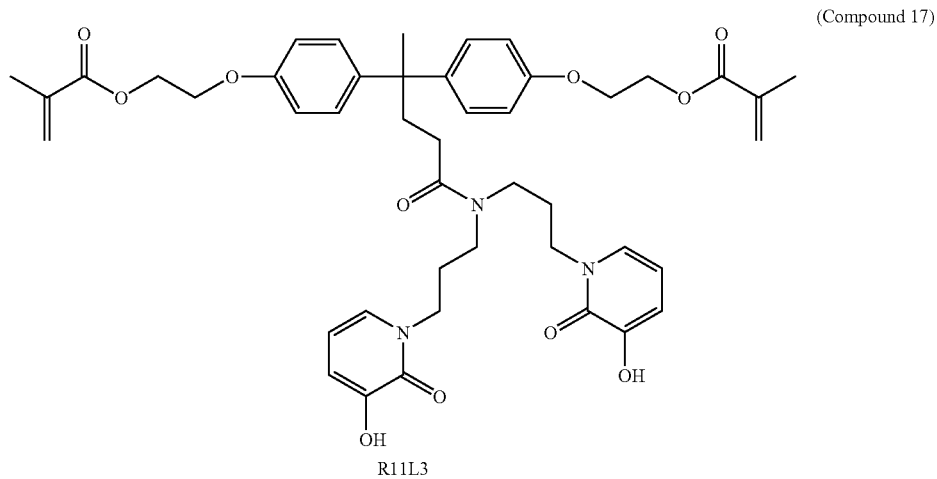

(Compound 17)

R11L3

To a stirred solution of compound 16 (2 mmol) in dichloromethane (5 mL), $BCl_3$ (5 ml, 5 mmol) was added slowly at 0° C. The mixture was then stirred at room temperature for 1.5 hours, and was monitored by ES-MS. The reaction mixture was filtered and diluted with dichloromethane (50 mL); washed with 5% $NaHCO_3$ (3×50 ml) and brine (1×50 ml). The collected organic layer was dried over sodium sulfate. The solvent was evaporated under vacuum, and the residue (compound 17) was purified by flash chromatography.

Analysis: ES-MS (negative ion, in methanol): m/z=810.2 ([M−H]$^-$, calculated: 810.37).

EXAMPLE 18

Synthesis of zirconium (IV) fluoride complex (fluoride-releasing monomer) R11L3-ZrF3H (Compound 18)

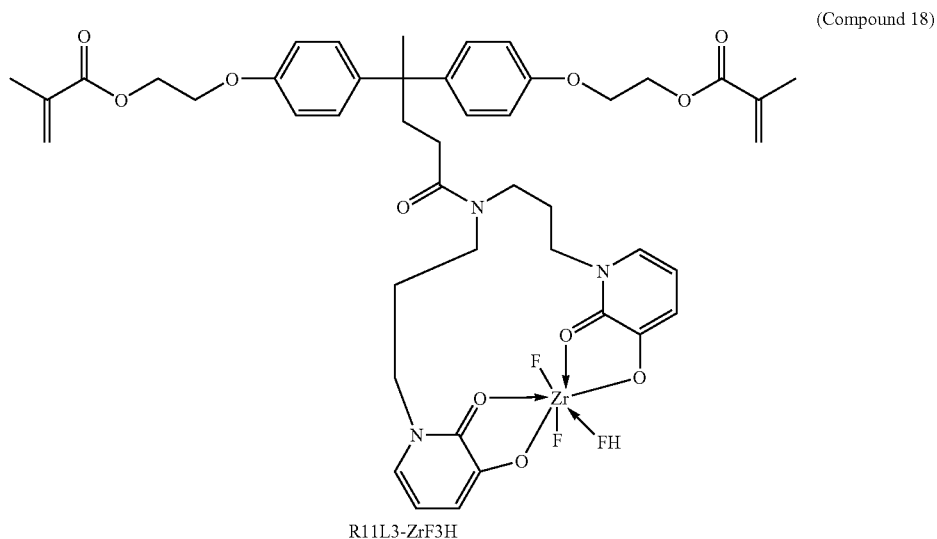

(Compound 18)

R11L3-ZrF3H

To a solution of Compound 17 (0.02 mmol) in MeOH (0.5 mL) was added $H_2ZrF_6$ (4.5 wt % solution in water, 90 μL, 0.02 mmol) with stirring at room temperature. After 20 minutes, the solvent was evaporated, and Compound 18 was obtained as a white solid. Analysis: ES-MS (negative ion in MeOH/$H_2O$): m/z=956.2, ([M–H]$^-$, calculated: 956.26), 936.1 ([M–H]$^-$, calculated 936.26).

EXAMPLE 19

Fabrication, Photopolymerization, Fluoride Release, Fluoride Recharge, and Microtensile Bonding Strength of a Prototype Self-Etching Primer, and a Prototype Bonding Agent An experimental bonding agent (Exp. Bond.) comprising two separate bottles of reagents was formulated as follows: Bottle A. Self-etching primer: To a mixture of synthesized monomer 3 (30 wt %), HEMA (30 wt %), acetone (30 wt %) and water (20 wt %) were added camphorquinone (0.02 wt % of the monomer), 1-phenyl-1,2-propane-dione (0.015 wt % of the monomer) and phenyl-bis(2,4,6-trimethylbenzoyl)phosphine oxide (PO) (0.015 wt % of the monomer).

Bottle B. Adhesive bonding agent: To a mixture of synthesized monomer 4 (30 wt %), HEMA (30 wt %), Bis-GMA (30 wt %) and UEDMA (10 wt %) were added camphorquinone (0.02 wt % of the monomer), 1-phenyl-1,2-propane-dione (0.015 wt % of the monomer) and phenyl-bis(2,4,6-trimethylbenzoyl)phosphine oxide (PO) (0.015 wt % of the monomer).

Two commercially-purchased bonding agents, which will be called Control-1 and Control-2, were also tested for comparison.

An experimental composite for testing fluoride-release was formulated using 70 wt % fluoroaluminosilicate filler (1.3 μm, Caulk/Dentsply) and 30 wt % monomer (BisGMA: EBPADMA:HDDMA 2:2:1). Disk specimens (d5×2 mm, n=5×8) were fabricated, coated with a bonding adhesive on the top surface, and light-cured for 20 sec. Other surfaces of the disk were coated with nail polish. The specimen was then immersed in 2 ml deionized water. Fluoride concentration was measured daily for 14 days using a fluoride ion-selective electrode. Then the specimens were recharged by applying "60 Seconds Taste Gel™," a topical fluoride agent (containing 1.23% w/w fluoride ion) for 1 min and rinsing with running deionized water for 1 min. Fluoride release from the recharged samples was measured daily for 4 days, and the recharge cycles were repeated three times. Microtensile bond strengths (MTBS) of the three bonding agents on ground enamel or dentin from extracted human teeth were tested on bar specimens (1×1 mm cross-section, n=10) after 24 h storage in distilled water at 37° C. The data were analyzed using ANOVA and post hoc tests. The results are shown in Table 1.

TABLE 1

Fluoride Release, Recharge, and Microtensile Bonding Strength (MTBS) of Experimental and Commercial Bonding Agents[a] (Mean ± SD)

| Property | Experimental Bond | Control-1 | Control-2 |
|---|---|---|---|
| Cumulative F-release over 14 days (μg/cm$^2$) | 46.7 ± 7.3 | 0.66 ± 0.22 | 5.30 ± 2.5 |
| Cumulative F-release 3 days after recharge (μg/cm$^2$) | 16.8 ± 12.6 | 2.12 ± 0.8 | 2.96 ± 1.9 |
| MTBS on enamel (MPa) | 23.7 ± 6.4 | 20.8 ± 5.97 | 16.4 ± 2.9 |
| MTBS on dentin (MPa) | 31.4 ± 6.7 | 34.2 ± 10.2 | 53.7 ± 11.6 |

[a]Self-etching primer contained 30 wt % monomer 3; bonding agent contained 30 wt % chelate 5.

As shown in Table 1, the experimental bonding agent provided substantially higher fluoride release and fluoride recharge (p<0.05). At the same time, its bonding strength on both enamel and dentin was similar to that of Control-1, which is one of the leading self-etching dental bonding agents currently on the market.

The complete disclosures of all references cited in this specification are hereby incorporated by reference. Also incorporated by reference are the entire disclosures of the following: (1) X. Xu, et al., "Synthesis of new fluoride-releasing dental monomer containing 1,2-hydroxypyridinones and zirconium fluoride complexes," Polymer Preprints (Proceedings of 231st ACS National Meeting, Atlanta, Ga., Mar. 26-30, 2006) 2006, 47(1), 337-338. (2) X. Xu, et al., "Synthesis Of New Chelating Monomers Containing Bis(Carboxymethyl)-L-Lysine and Their Zirconium Fluoride Complexes," Polymer Preprints (Proceedings of 231st ACS National Meeting, Atlanta, Ga., Mar. 26-30, 2006) 2006, 47(1), 335-336. (3) X. Xu, et al., "Synthesis of new fluoride-releasing dental monomer containing 1,2-hydroxypyridinones and zirconium fluoride complexes," Abstract, 231st ACS National Meeting, Atlanta, Ga., Mar. 26-30, 2006. (4) X. Xu, et al., "Synthesis Of New Chelating Monomers Containing Bis(Carboxymethyl)-L-Lysine and Their Zirconium Fluoride Complexes," Abstract, 231st ACS National Meeting, Atlanta, Ga., March 26-30, 2006.

What is claimed:

1. A compound having the structure

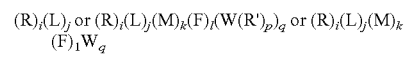

wherein R has structure R11:

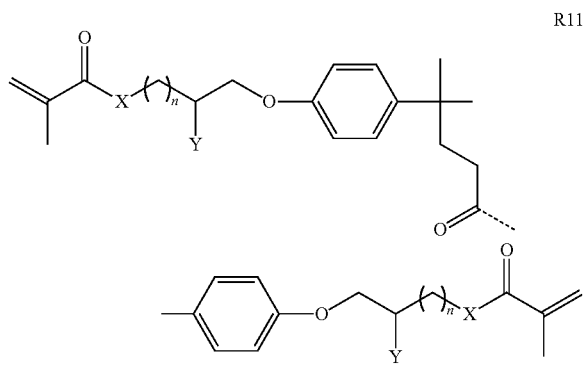

and wherein
L is selected from the group consisting of the following structures L1 to L3, L5 to L10, and L12 to L15:

35
L1
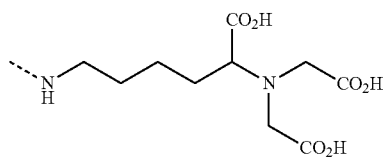
L2
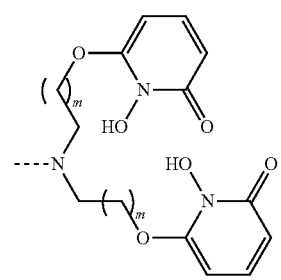
L3
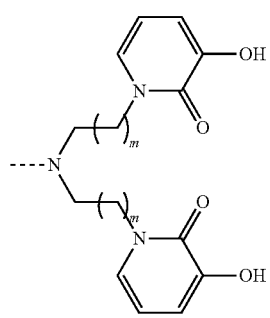
L5
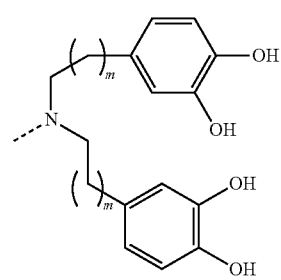
L6
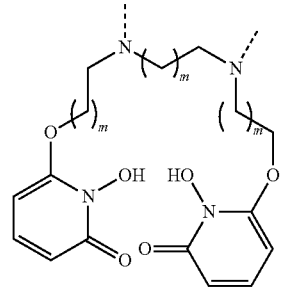
-continued
L7
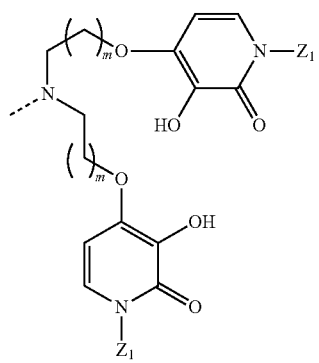
L8
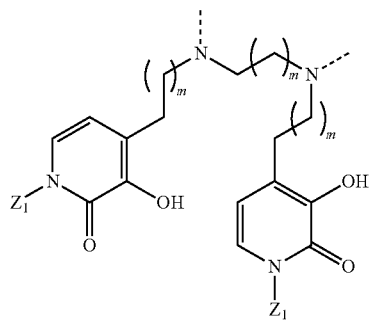
L9
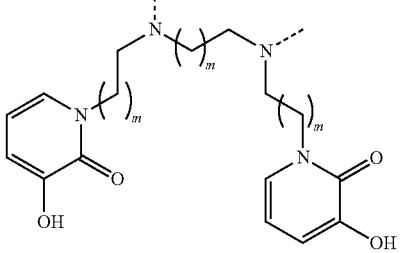
L10
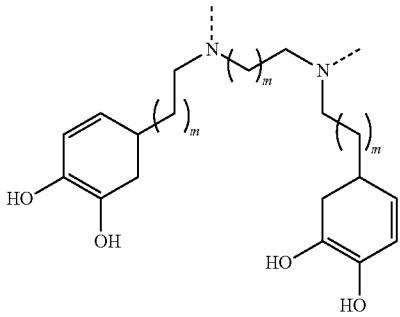

-continued

L12
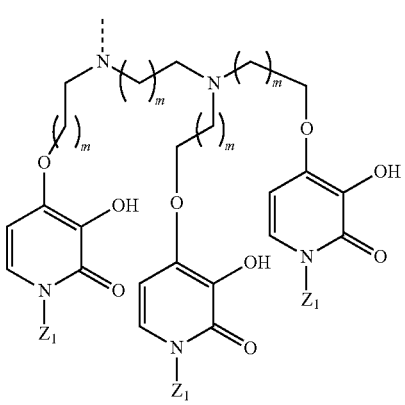

L13
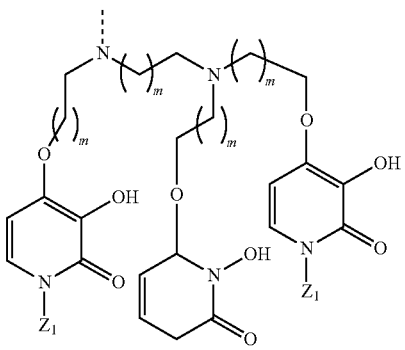

L14
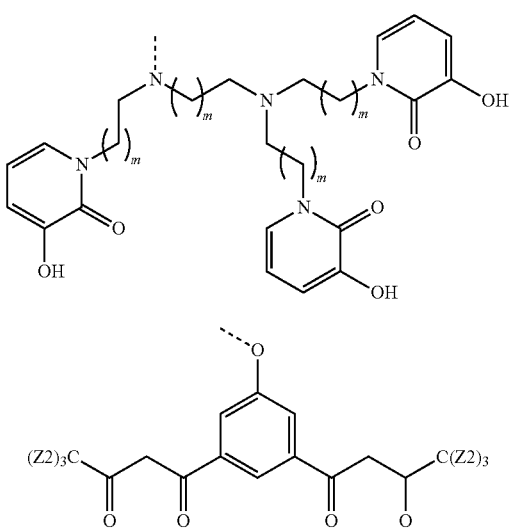

L15 wherein:
M is a metal atom having a valence of +2 or greater;
i is an integer from 1 to 4;
j is an integer from 1 to 4;
k is an integer from 1 to 4;
l is an integer from 1 to 4;
F is one or more fluoride atoms;

W or W(R')$_p$ is a counter-ion that maintains the neutrality of the compound; wherein W is selected from the group consisting of hydrogen, an alkali metal ion, and ammonium; and wherein W(R')$_p$ is selected from the group consisting of $C_1$ to $C_{50}$ substituted or unsubstituted quaternary ammonium ions, and $C_1$ to $C_{50}$ substituted or unsubstituted pyridinium ions;

each R' is a substituted or unsubstituted aliphatic or aromatic group comprising 1 to 50 carbon atoms, wherein at least one of the R' groups comprises at least one polymerizable group; and wherein the various R' groups can be the same or different; and wherein p is an integer from 0 to 4;

q is an integer from 0 to 4;

a dotted line represents the position of a bond between R and L;

X is an ether —O— linkage or an —NH— linkage; and the various X moieties may be the same or different;

Y is hydrogen; or a hydroxyl group; or a half ester of a diacid or triacid selected from the group consisting of phosphoric acid, oxalic acid, malonic acid, maleic acid, a disubstituted maleic acid, succinic acid, fumaric acid, malic acid, tartaric acid, glutaric acid, glutaconic acid, adipic acid, pimelic acid, cyclohexen-1,2-diacid, (o, m, or p)-phthalic acid, citric acid, hydroxyphthalic acid, suberic acid, trimellitic acid, and sebaric acid; or wherein Y is a salt of such a diacid or triacid; and the various Y moieties may be the same or different;

$Z_1$ is hydrogen or a substituted or unsubstituted alkyl group comprising 1 to 4 carbon atoms; and the various $Z_1$ moieties may be the same or different;

$Z_2$ is hydrogen, fluoride, or a substituted or unsubstituted alkyl group comprising 1 to 4 carbon atoms; and the various $Z_2$ moieties may be the same or different;

n is an integer from 0 to 6; and the various values for the parameter n may be the same or different; and m is an integer from 0 to 6; and the various values for the parameter m may be the same or different.

2. A compound as recited in claim 1, wherein M is selected from the group consisting of Sn, Zn, Sr, Al, La, Sb, Yb, Ti, Zr, Ce, and Th.

3. A compound as recited in claim 1, wherein M comprises $Zr^{+4}$.

4. A compound as recited in claim 1, wherein M comprises $Zr^{+4}$, and wherein one or more fluoride ions is coordinated to said $Zr^{+4}$.

5. A compound as recited in claim 1, wherein one or more fluoride ions is coordinated to said M.

6. A compound as recited in claim 1, wherein said compound has the structure (R)$_i$(L)$_j$(M)$_k$(F)$_l$(W(R')$_p$)$_q$; wherein at least one R' moiety is selected from the group consisting of $C_8$ to $C_{24}$ substituted or unsubstituted alkyl groups; and wherein at least two R' moieties are each selected from the group consisting of substituted or unsubstituted methyl and ethyl groups.

7. A compound as recited in claim 1, wherein said compound is selected from the group consisting of Compounds 17, 18, 19 20, and 21, whose respective structures are as follows:
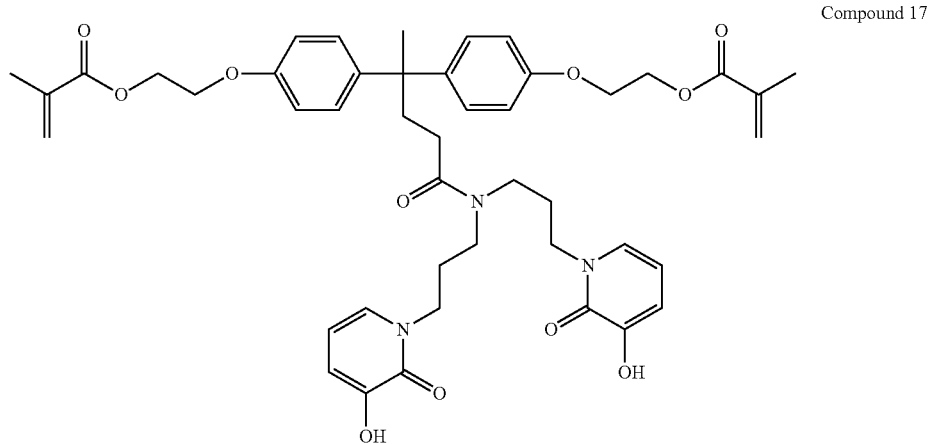
Compound 17
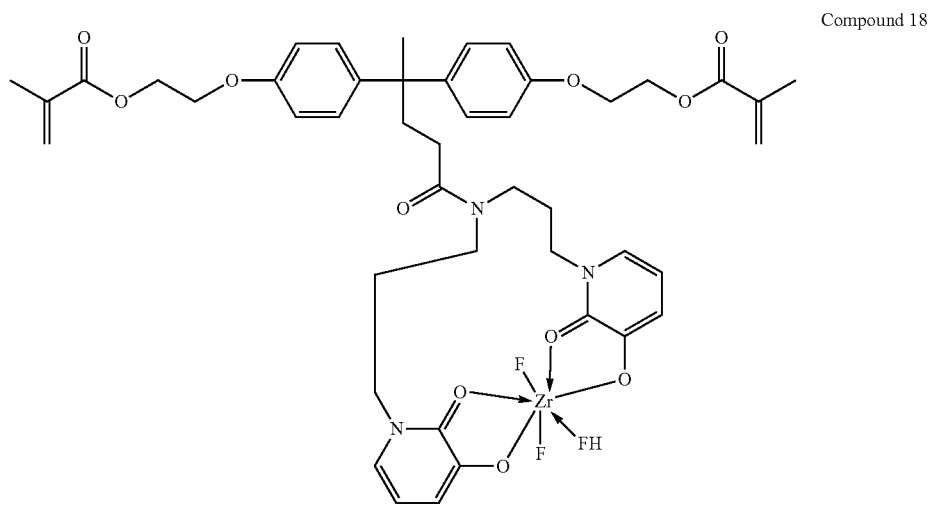
Compound 18
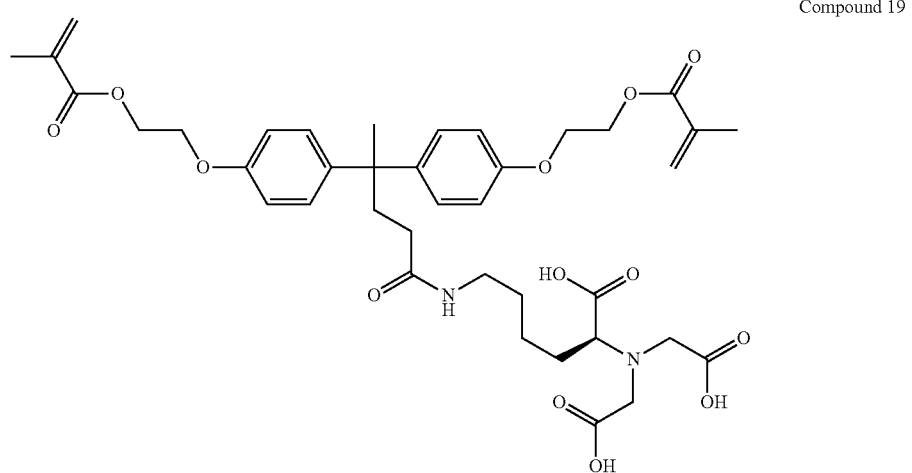
Compound 19

-continued
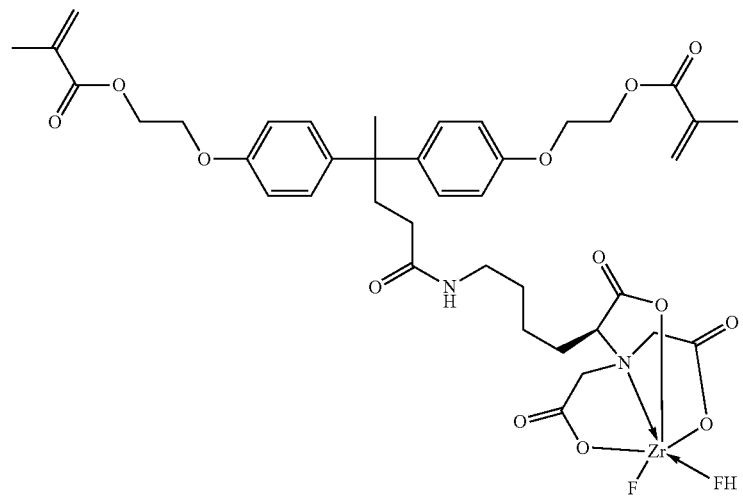
Compound 20
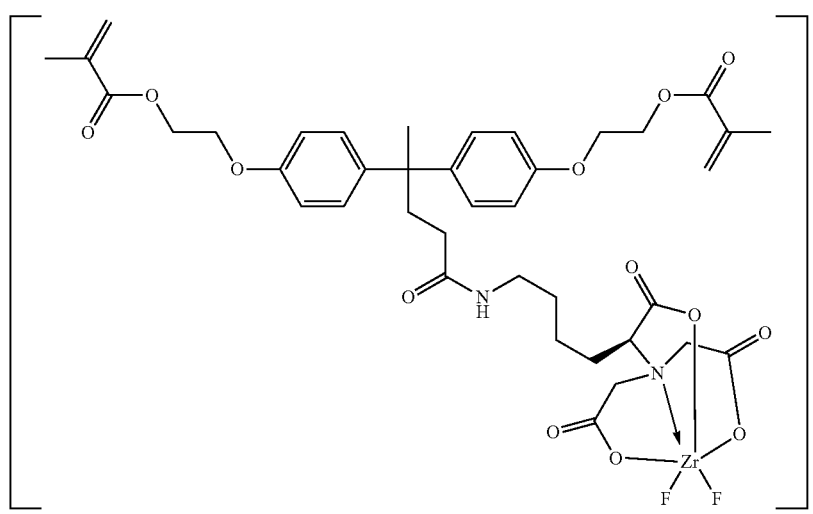
Compound 21
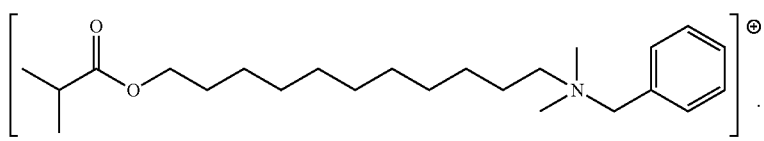
8. A compound as recited in claim 7, wherein said compound is Compound 17.
9. A compound as recited in claim 7, wherein said compound is Compound 18.
10. A compound as recited in claim 7, wherein said compound is Compound 19.
11. A compound as recited in claim 7, wherein said compound is Compound 20.
12. A compound as recited in claim 7, wherein said compound is Compound 21.
* * * * *